US 11,416,984 B2

(12) United States Patent
Takeshima et al.

(10) Patent No.: US 11,416,984 B2
(45) Date of Patent: Aug. 16, 2022

(54) MEDICAL IMAGE PROCESSING APPARATUS, MEDICAL IMAGE GENERATION APPARATUS, MEDICAL IMAGE PROCESSING METHOD, AND STORAGE MEDIUM

(71) Applicant: CANON MEDICAL SYSTEMS CORPORATION, Otawara (JP)

(72) Inventors: Hidenori Takeshima, Kawasaki (JP); Masao Yui, Otawara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 270 days.

(21) Appl. No.: 16/543,669

(22) Filed: Aug. 19, 2019

(65) Prior Publication Data
US 2020/0065964 A1  Feb. 27, 2020

(30) Foreign Application Priority Data

Aug. 21, 2018  (JP) .............................. JP2018-154590

(51) Int. Cl.
*G06T 7/00* (2017.01)
*A61B 6/03* (2006.01)
*A61B 5/055* (2006.01)
*G01T 1/164* (2006.01)
*G01T 1/20* (2006.01)
*G06N 3/02* (2006.01)

(52) U.S. Cl.
CPC ............ *G06T 7/0012* (2013.01); *A61B 6/032* (2013.01); *G01T 1/20* (2013.01); *G06N 3/02* (2013.01); *A61B 5/055* (2013.01); *G01T 1/1645* (2013.01); *G06T 2207/20081* (2013.01); *G06T 2207/20084* (2013.01); *G06T 2207/30004* (2013.01)

(58) Field of Classification Search
None
See application file for complete search history.

(56) References Cited

U.S. PATENT DOCUMENTS 9,188,655 B2 * 11/2015 Takeshima ......... G01R 33/5608
10,393,842 B1 * 8/2019 Cheng ................ G01R 33/5611
(Continued)

OTHER PUBLICATIONS

K-Space Deep Learning for Accelerated MRI; Yoseo Han, Leonard Sunwoo , and Jong Chul Ye , Senior Member, IEEE Jul. 2019 (Year: 2019).*

(Continued)

*Primary Examiner* — Nancy Bitar
(74) *Attorney, Agent, or Firm* — Oblon, McClelland, Maier & Neustadt, L.L.P.

(57) ABSTRACT

According to one embodiment, a medical image processing apparatus includes an acquirer, a first processor and a second processor. The acquirer is configured to acquire nonequispaced sampled data from a test object. The first processor is configured to derive product-sums of the nonequispaced sampled data acquired by the acquirer and a plurality of coefficient sets and generate equispaced sampled data including a plurality of elements with which the product-sums derived for the coefficient sets are associated as element values. The second processor is configured to generate a medical image in which at least part of the test object has been imaged through reconstruction basis on the equispaced sampled data generated by the first processor.

11 Claims, 14 Drawing Sheets

(56) References Cited

U.S. PATENT DOCUMENTS

| | | | |
|---|---|---|---|
| 11,037,027 B2* | 6/2021 | Sallee | G06N 3/0472 |
| 2013/0285662 A1* | 10/2013 | Takeshima | G01R 33/34 |
| | | | 324/318 |
| 2015/0369893 A1* | 12/2015 | Takeshima | G01R 33/54 |
| | | | 324/309 |
| 2017/0102827 A1* | 4/2017 | Christiansson | G06F 3/0421 |
| 2019/0336033 A1* | 11/2019 | Takeshima | G01R 33/5608 |
| 2019/0369190 A1* | 12/2019 | Ye | G06N 20/10 |

OTHER PUBLICATIONS

Bo Zhu et al., "Image reconstruction by domain-transform manifold learning." Nature vol. 555, pp. 487-492 (Mar. 22, 2018): doi:10.1038/nature25988.

* cited by examiner

| SAMPLE POINT | ASSUMED POSITION OF SAMPLE POINT | COEFFICIENT SEQUENCE |
|---|---|---|
| $S_1$ | $P_1$ | $C_1$ |
| $S_2$ | $P_2$ | $C_2$ |
| $S_3$ | $P_3$ | $C_3$ |
| ... | ... | ... |
| ... | ... | ... |
| $S_{n-1}$ | $P_{n-1}$ | $C_{n-1}$ |
| $S_n$ | $P_n$ | $C_n$ |

MEDICAL IMAGE PROCESSING APPARATUS, MEDICAL IMAGE GENERATION APPARATUS, MEDICAL IMAGE PROCESSING METHOD, AND STORAGE MEDIUM

CROSS-REFERENCE TO RELATED APPLICATION

The present application claims priority based on Japanese Patent Application No. 2018-154590, filed on Aug. 21, 2018, the content of which is incorporated herein by reference.

FIELD

Embodiments described herein relate generally to a medical image processing apparatus, a medical image generation apparatus, a medical image processing method, and a storage medium.

BACKGROUND

A technology for reconstructing medical images using a deep neural network, called an auto map, is known.

In the conventional technology, the accuracy of reconstruction of a medical image is not sufficient and the picture quality of a medical image generated according to reconstruction is not satisfactory because a deep neural network is caused to learn all calculations necessary for reconstruction of non-Cartesian data.

DETAILED DESCRIPTION

According to one embodiment, a medical image processing apparatus includes an acquirer, a first processor and a second processor. The acquirer acquires nonequispaced sampled data from a test object. The first processor derives product-sums of the nonequispaced sampled data acquired by the acquirer and a plurality of coefficient sets and generates equispaced sampled data including a plurality of elements with which the product-sums derived for the coefficient sets are associated as element values. The second processor generates a medical image in which at least part of the test object has been imaged through reconstruction basis on the equispaced sampled data generated by the first processor.

Hereinafter, embodiments of a medical image processing apparatus, a medical image generation apparatus, a medical image processing method, and a storage medium will be described in detail.

First Embodiment

Figure 1:
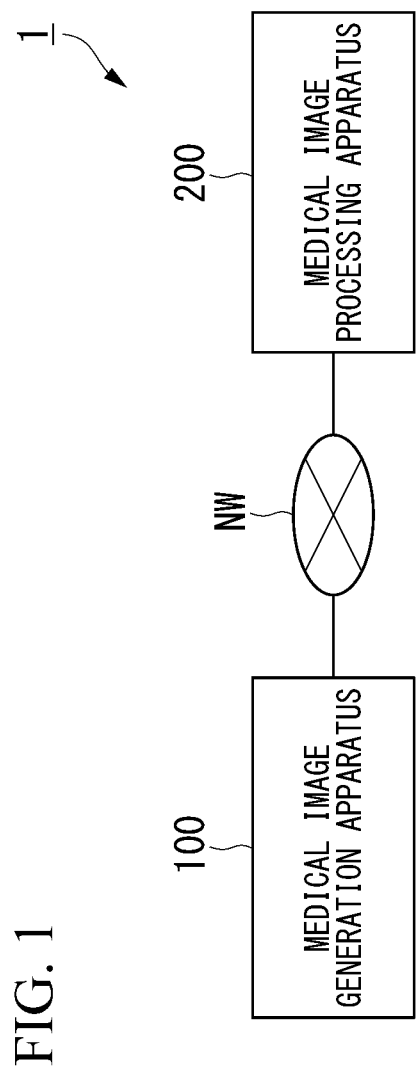
FIG. 1 is a diagram showing an example of a configuration of a medical image processing system including a medical image processing apparatus according to a first embodiment.

FIG. 1 is a diagram showing an example of a configuration of a medical image processing system 1 including a medical image processing apparatus 200 according to a first embodiment. For example, the medical image processing system 1 includes a medical image generation apparatus 100 and the medical image processing apparatus 200, as shown in FIG. 1. The medical image generation apparatus 100 and the medical image processing apparatus 200 are connected through a network NW. Examples of the network NW includes a wide area network (WAN), a local area network (LAN), the Internet, a dedicated line, a wireless base station, a provider, and the like.

Examples of the medical image generation apparatus 100 include a magnetic resonance imaging (MRI) apparatus, a computed tomography (CT) apparatus, and the like. For example, an MRI apparatus is an apparatus that generates a medical image (MR image) by applying magnetic fields to a test object (e.g., a human body), receiving electromagnetic waves generated from hydrogen nuclei in the test object according to nuclear magnetic resonance using a coil and reconstructing a signal based on the received electromagnetic waves. For example, the CT apparatus is an apparatus that generates a medical image (CT image) by radiating X rays to a test object from an X-ray tube rotating around the test object, detecting X rays that have passed through the test object and reconstructing a signal based on the detected X rays.

In the following description, the medical image generation apparatus 100 is described as an MRI apparatus as an example.

The medical image processing apparatus 200 is implemented as one or a plurality of processors. For example, the medical image processing apparatus 200 may be a computer included in a cloud computing system or a computer (stand-alone computer) operating alone independently of other apparatuses.

[Example of Configuration of Medical Image Generation Apparatus (MRI Apparatus)]

Figure 2:
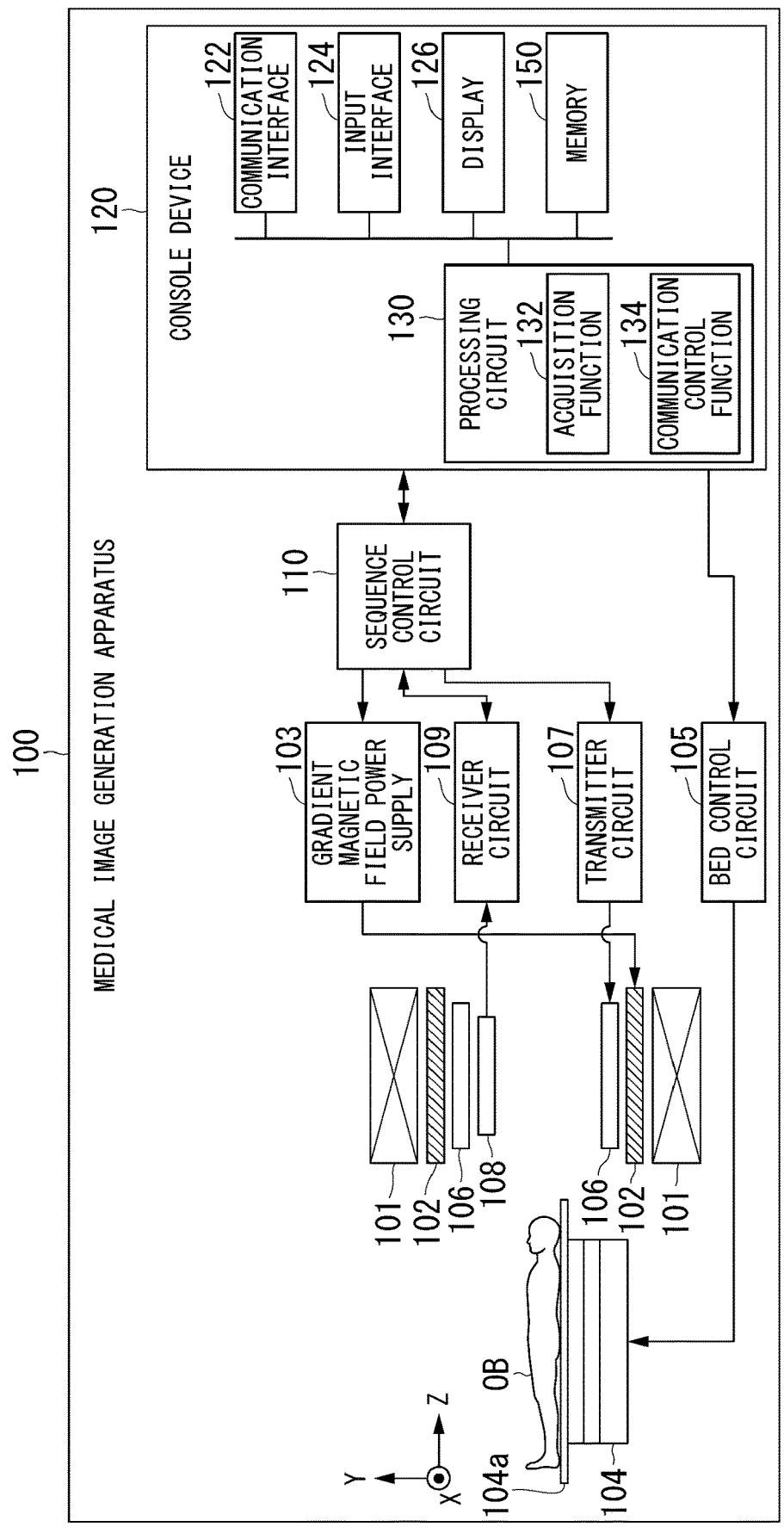
FIG. 2 is a diagram showing an example of a medical image generation apparatus according to the first embodiment.

FIG. 2 is a diagram showing an example of the medical image generation apparatus 100 according to the first embodiment. As shown in FIG. 2, the medical image generation apparatus 100 includes a static magnetic field magnet 101, a gradient magnetic field coil 102, a gradient magnetic field power supply 103, a bed 104, a bed control circuit 105, a transmission coil 106, a transmitter circuit 107, a reception coil 108, a receiver circuit 109, a sequence control circuit 110, and a console device 120.

The static magnetic field magnet 101 is a magnet formed in a hollow approximately cylindrical shape and generates a uniform static magnetic field in an inner space. For example, the static magnetic field magnet 101 is a permanent magnet, a superconducting magnet or the like.

The gradient magnetic field coil 102 is a coil formed in a hollow approximately cylindrical shape and is provided inside the static magnetic field magnet 101. The gradient magnetic field coil 102 is a combination of three coils corresponding to x, y and z axes orthogonal to one another. The z-axis direction represents a longitudinal direction of a top plate 104a of the bed 104, the x-axis direction represents an axial direction perpendicular to the z-axis direction and parallel with the floor of a room in which the medical image generation apparatus 100 is installed, and the y-axis direction represents an axial direction perpendicular to the floor. The three coils corresponding to the axial directions are individually provided with a current from the gradient magnetic field power supply 103 and generate gradient magnetic fields whose magnetic field intensity changes along the respective x, y and z axes. The z-axis direction is the same direction as static magnetic fields.

The gradient magnetic field power supply 103 supplies a current to the gradient magnetic field coil 102. Here, gradient magnetic fields of the x, y and z axes generated by the gradient magnetic field coil 102 respectively correspond to, for example, a slice selection gradient magnetic field Gs, a phase encoding gradient magnetic field Ge, and a readout gradient magnetic field Gr. The slice selection gradient magnetic field Gs is used to determine an imaging slice at will. The phase encoding gradient magnetic field Ge is used to change the phase of a magnetic resonance signal in accordance with the spatial position. The readout gradient magnetic field Gr is used to change the frequency of a magnetic resonance signal in accordance with the spatial position.

The bed 104 includes a top plate 104a on which a test object OB is placed, and the top plate 104a is inserted into a hollow space (image capture opening) of the gradient magnetic field coil 102 under the control of the bed control circuit 105 while the test object OR is placed thereon. In general, the bed 104 is installed in such a manner that the longitudinal direction thereof extends parallel to the central axis of the static magnetic field magnet 101. The bed control circuit 105 drives the bed 104 to move the top plate 104a in the longitudinal direction and vertical direction under the control of the console device 120.

The transmission coil 106 is provided inside the gradient magnetic field coil 102, receives a supply of a radio frequency (RF) pulse from the transmitter circuit 107 and generates a radio frequency magnetic field. The transmitter circuit 107 supplies the transmission coil 106 with the RF pulse corresponding to a Larmor frequency determined by the type of a targeted atom and intensities of magnetic fields.

The reception coil 108 is provided inside the gradient magnetic field coil 102 and receives magnetic resonance signals emitted from the test object OB due to an influence of the radio frequency magnetic field. When the reception coil 108 has received the magnetic resonance signals, the reception coil 108 outputs the received magnetic resonance signals to the receiver circuit 109. The reception coil 108 is a coil array having one or more, typically a plurality of, reception coils in the first embodiment. Hereinafter, when the reception coil is a coil array (multi-coil), each coil constituting the array will be referred to as a coil element.

The receiver circuit 109 generates magnetic resonance data basis on the magnetic resonance signals output from the reception coil 108. Specifically, the receiver circuit 109 generates the magnetic resonance data that is a digital signal by performing a Fourier transform on the magnetic resonance signals output from the reception coil 108. In addition, the receiver circuit 109 transmits the generated magnetic resonance data to the sequence control circuit 110. The receiver circuit 109 may be provided on the side of a gantry device including the static magnetic field magnet 101, the gradient magnetic field coil 102 and the like. Magnetic resonance signals output from the respective coil elements of the reception coil 108 are appropriately distributed and combined and output to the receiver circuit 109. The reception coil 108 and the receiver circuit 109 are an example of a "generator."

The sequence control circuit 110 images the test object OB by driving the gradient magnetic field power supply 103, the transmitter circuit 107 and the receiver circuit 109 basis on sequence information transmitted from the console device 120. The sequence information is information defining a procedure for performing an imaging process. The sequence information includes information defining the intensity of power supplied from the gradient magnetic field power supply 103 to the gradient magnetic field coil 102, a timing at which the power is supplied, the intensity of an RF pulse transmitted from the transmitter circuit 107 to the transmission coil 106, a timing at which the RF pulse is applied, a tuning at which the receiver circuit 109 detects magnetic resonance signals, and the like.

Further, the sequence control circuit 110 images the test object OB by driving the gradient magnetic field power supply 103, the transmitter circuit 107 and the receiver circuit 109, and when magnetic resonance data has been received from the receiver circuit 109, transfers the received magnetic resonance data to the console device 120.

The console device 120 performs overall control of the medical image generation apparatus 100 or collects magnetic resonance data. For example, the console device 120 includes a communication interface 122, an input interface 124, a display 126, a processing circuit 130, and a memory (storage) 150.

For example, the communication interface 122 includes a communication interface such as a network interface card (NIC). The communication interface 122 communicates with the medical image processing apparatus 200 through the network NW and receives information from the medical image processing apparatus 200. The communication interface 122 outputs the received information to the processing circuit 130. Further, the communication interface 122 may transmit information to other devices connected through the network NW under the control of the processing circuit 130.

The input interface 124 receives various input operations from an operator, converts the received input operations into electrical signals and outputs the electrical signals to the processing circuit 130. For example, the input interface 124 is implemented as a mouse, a keyboard, a track ball, a switch, a button, a joystick, a touch panel or the like. In addition, the input interface 124 may be implemented as a user interface that receives voice input, such as a microphone, for example. When the input interface 124 is a touch panel, the display 126 which will be described later may be integrated with the input interface 124.

The display 126 displays various types of information. For example, the display 126 displays images generated by the processing circuit 130, a graphical user interface (GUI) for receiving various input operations from an operator, and the like. For example, the display 126 is a liquid crystal display (LCD), a cathode ray tube (CRT) display, an organic electroluminescence (EL) display, or the like.

The processing circuit 130 executes an acquisition function 132 and a communication control function 134, for example. These functions (components) are implemented as a hardware processor (or a processor circuit) such as a central processing unit (CPU) or a graphics processing unit (GPU) executing a program (software) stored in the memory 150. Further, some or all of the functions of the processing circuit 130 may be implemented as hardware (circuitry) such as a large scale integration (LSI) circuit, an application specific integrated circuit (ASIC) and a field-programmable gate array (FPGA) or software and hardware in cooperation. In addition, the aforementioned program may be stored in the memory 150 in advance or stored in a detachable storage medium such as a DVD or a CD-ROM and installed in the memory 150 from the storage medium by mounting the storage medium in a drive device of the console device 120.

The memory 150 is implemented as a semiconductor memory element such as a random-access memory (RAM) or a flash memory, a hard disk, an optical disc, or the like. These non-transient storage media may be implemented as other storage devices connected through the network NW, such as a network attached storage (NAS) and an external storage device. Further, the memory 150 may include a transient storage medium such as a read only memory (ROM) or a register.

The acquisition function 132 acquires magnetic resonance data from the sequence control circuit 110. The magnetic resonance data is data acquired by performing a Fourier transform on an electromagnetic wave signal (nuclear magnetic resonance signal) generated in the test object OB according to nuclear magnetic resonance, as described above. In the following description, the magnetic resonance data is referred to as "k-space data Dk." A k space represents a space (a space in which the k-space data Dk is arranged) in which one-dimensional waveforms are collected when nuclear magnetic resonance signals are repeatedly collected by the reception coil 108 as the one-dimensional waveforms.

Figure 3:
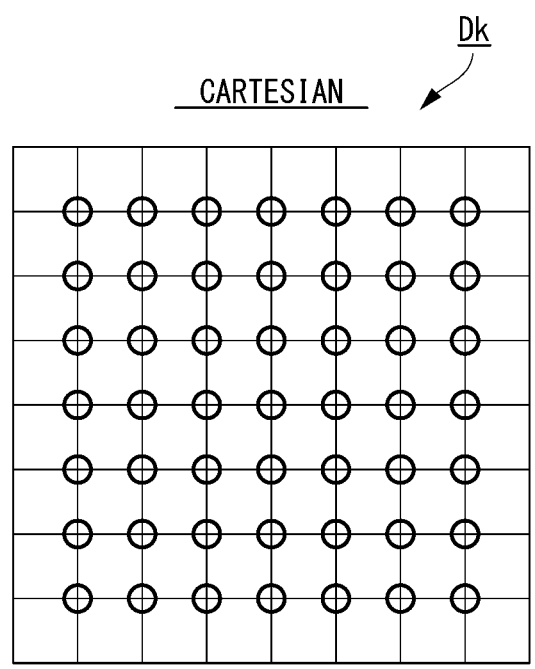
FIG. 3 is a diagram showing an example of k-space data.
Figure 4:
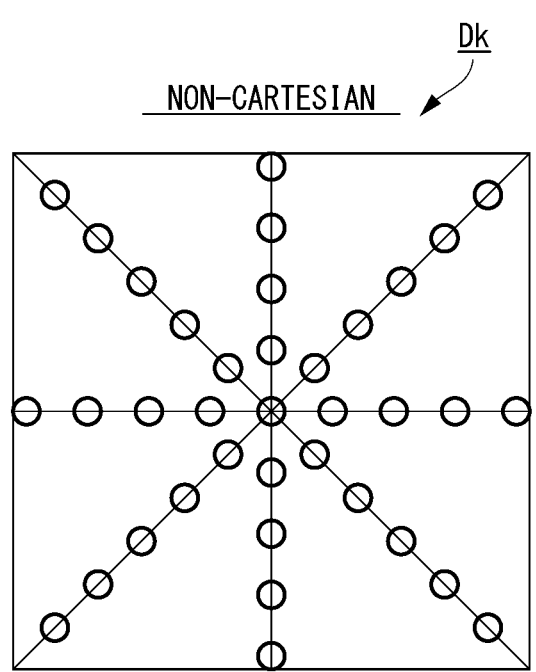
FIG. 4 is a diagram showing an example of k-space data.
Figure 5:
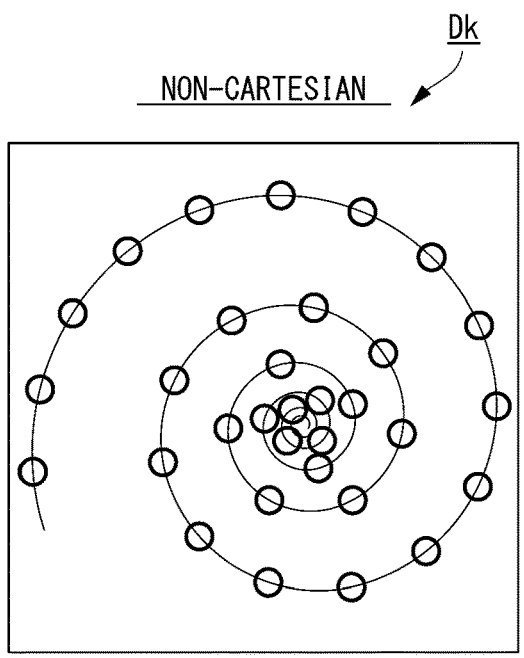
FIG. 5 is a diagram showing an example of k-space data.

FIG. 3 to FIG. 5 are diagrams showing examples of k-space data Dk. FIG. 3 shows k-space data Dk in which sample points representing sampled magnetic resonance data (an example of sample data) are present in a grid form in the k space represented by the rectangular coordinate system (Cartesian coordinate system) in which x, y and z axes are orthogonal to one another. This k-space data is obtained when nuclear magnetic resonance signals have been collected at a certain time interval (period). On the other hand, FIG. 4 and FIG. 5 show k-space data Dk in which sample points are present in a non-uniform manner in the k space. The k-space data Dk shown in FIG. 4 is obtained by radially scanning (radial-scanning) the test object OB centering around a sample point at which the signal strength of a nuclear magnetic resonance signal is high, and the k-space data Dk shown in FIG. 5 is obtained by spirally scanning (spiral-scanning) the test object OB centering around a sample point at which the signal strength of a nuclear magnetic resonance signal is high. It is possible to improve robustness against noise and increase a processing speed by radially scanning or spirally scanning the test object OB in this manner. However, when the test object OB is radially scanned or spirally scanned, k-space data Dk in which sample points are not arranged in a grid form in the k space is obtained.

In the present embodiment, when sample points are disposed at positions corresponding one-to-one to output points arranged in a grid form in a certain space, data of the sample points is defined as "Cartesian data." When sample points are not disposed at positions corresponding one-to-one to output points arranged in a grid form, data of the sample points is defined as "non-Cartesian data." An output point is a point corresponding to a pixel of a reconstructed image. Particularly, a description will be provided on the assumption that k-space data Dk in which sample points are arranged in a grid form in the k space as shown in FIG. 3 is referred to as "Cartesian k-space data Dk" and k-space data Dk in which sample points are not arranged in a grid form in the k space as shown in FIGS. 4 and 5 is referred to as "non-Cartesian k-space data Dk." The Cartesian data is an example of an "equispaced sampled data." The non-Cartesian data is an example of an "nonequispaced sampled data."

Since sample points are arranged with regularity in the k space in the Cartesian k-space data Dk, a period between samples is uniform and all sample points can be inversely Fourier transformed according to the same sampling spatial frequency. On the other hand, sample points are not arranged with regularity in the k space in the non-Cartesian k-space data Dk, and thus noise called an artifact may be included in a reconstructed image when a process corresponding to an inverse Fourier transform is performed.

When the medical image generation apparatus 100 images the test object OB at a higher speed by thinning and collecting the k-space data Dk with respect to a certain axial direction using a half-Fourier method, for example, the k-space data Dk becomes sparse (thinned) data in the k space.

When the k-space data Dk has been acquired through the acquisition function 132, the communication control function 134 causes the communication interface 202 to communicate with the medical image processing apparatus 200 to transmit the k-space data Dk to the medical image processing apparatus 200 which is the communication partner. In addition, the communication control function 134 causes the communication interface 202 to communicate with the medical image processing apparatus 200 to acquire a reconstructed image from the medical image processing apparatus 200 which is the communication partner. When the reconstructed image is acquired, the communication control function 134 may output the reconstructed image to the display 126. Accordingly, the reconstructed image is displayed on the display 126.

[Example of Configuration of Medical Image Processing Apparatus]

Figure 6:
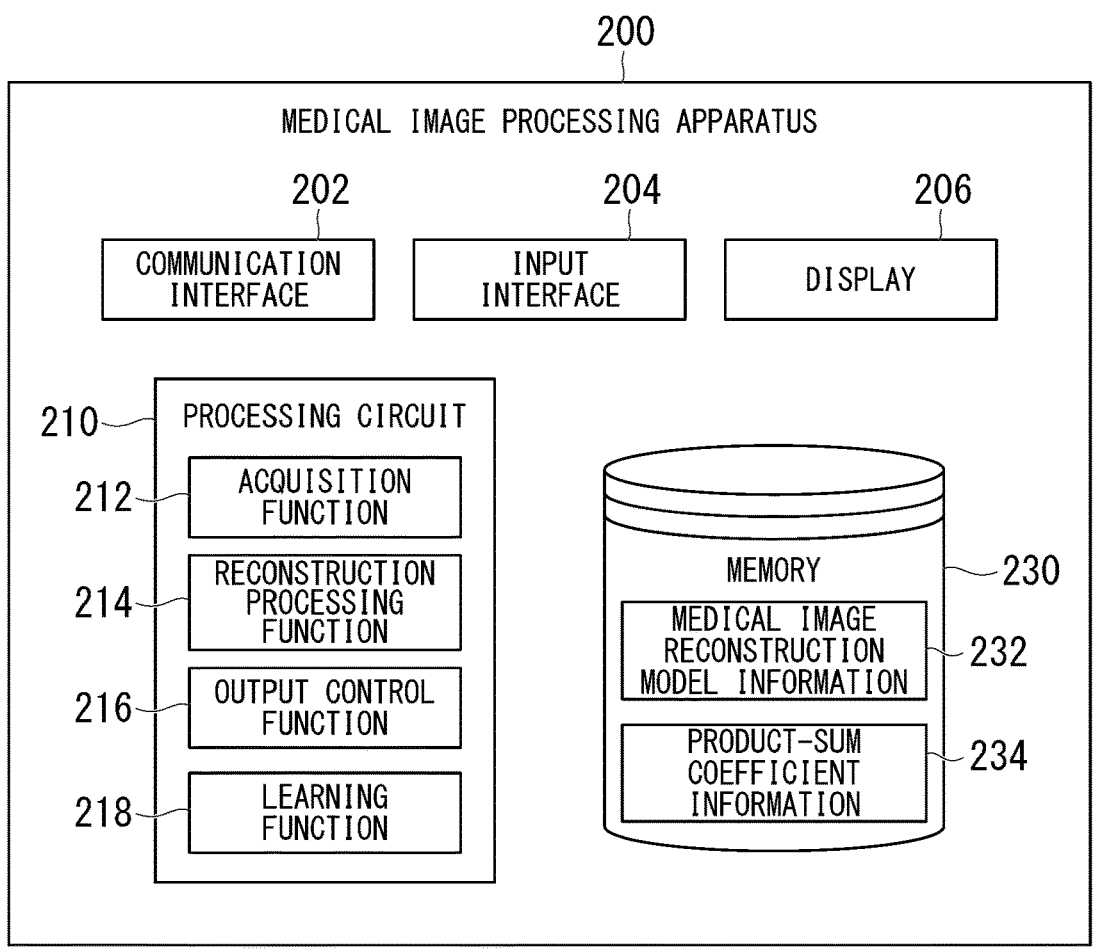
FIG. 6 is a diagram showing an example of the medical image processing apparatus according to the first embodiment.

FIG. 6 is a diagram showing an example of the medical image processing apparatus 200 according to the first embodiment. As shown in FIG. 6, the medical image processing apparatus 200 includes a communication interface 202, an input interface 204, a display 206, a processing circuit 210 and a memory 230, for example.

The communication interface 202 includes a communication interface such as an NIC, for example.

The communication interface 202 communicates with the medical image generation apparatus 100 through the network NW and receives information from the medical image generation apparatus 100. The communication interface 202 outputs the received information to the processing circuit 210. Further, the communication interface 202 may transmit information to other devices connected through the network NW under the control of the processing circuit 210. The other devices may be terminal devices which can be used by image readers such as doctors and nurses, for example.

The input interface 204 receives various input operations from an operator, converts the received input operations into electrical signals and outputs the electrical signals to the processing circuit 210. For example, the input interface 204 is implemented as a mouse, a keyboard, a track ball, a switch, a button, a joystick, a touch panel, or the like. In addition, the input interface 204 may be implemented as a user interface that receives voice input, such as a microphone, for example. When the input interface 204 is a touch panel, the display 206 which will be described later may be integrated with the input interface 204.

The display 206 displays various types of information. For example, the display 206 displays images (reconstructed images which will be described later) generated by the processing circuit 210, a GUI for receiving various input operations from an operator, and the like. For example, the display 206 is an LCD, a CRT display, an organic EL display, or the like.

The processing circuit 210 executes an acquisition function 212, a reconstruction processing function 214, an output control function 216, and a learning function 218, for example. The acquisition function 212 is an example of an "acquirer."

These functions (components) are implemented as a hardware processor (or a processor circuit) such as a CPU or a GPU executing a program (software) stored in the memory 230. Further, some or all of these functions may be implemented as hardware (circuitry) such as an LSI circuit, an ASIC and an FPGA or software and hardware in cooperation. In addition, the aforementioned program may be stored in the memory 230 in advance or stored in a detachable storage medium such as a DVD or a CD-ROM and installed in the memory 230 from the storage medium by mounting the storage medium in a drive device of the medical image processing apparatus 200.

The memory 230 is implemented as a semiconductor memory element such as a RAM or a flash memory, a hard disk, an optical disc, or the like. These non-transient storage media may be implemented as other storage devices connected through the network NW, such as a NAS and an external storage device. Further, the memory 230 may include a transient storage medium such as a ROM or a register. For example, medical image reconstruction model information 232, product-sum coefficient information 234 and the like are stored in the memory 230. This information will be described later.

The acquisition function 212 causes the communication interface 202 to communicate with the medical image generation apparatus 100 to acquire k-space data Dk from the medical image generation apparatus 100 which is the communication partner. Hereinafter, a description will be provided on the assumption that the k-space data Dk acquired according to the acquisition function 212 is non-Cartesian k-space data Dk.

The reconstruction processing function 214 reconstructs a medical image (MR image) from the non-Cartesian k-space data Dk acquired through the acquisition function 212 according to a medical image reconstruction model 300 represented by the medical image reconstruction model information 232. The non-Cartesian k-space data Dk acquired through the acquisition function 212 is represented, for example, by a vector having each sample point as an element. Although the vector of the non-Cartesian k-space data Dk is a vector having two or more elements in most cases, the present invention is not limited thereto and the vector may be a vector having one element.

The medical image reconstruction model information 232 is information (a program or a data structure) defining the medical image reconstruction model 300. For example, each function of the medical image reconstruction model 300 may be implemented as a part of the reconstruction processing function 214 by a processor executing the medical image reconstruction model information 232. The medical image reconstruction model 300 includes one or more deep neural networks (DNNs), for example.

For example, the medical image reconstruction model information 232 includes connection information representing how units included in an input layer, one or more hidden layers (middle layers) and an output layer constituting each DNN included in the medical image reconstruction model 300 are connected, weight information representing the number of connection coefficients assigned to data input and output between connected units, and the like. The unit includes a activation function, a weight coefficient, and the like.

For example, the connection information includes information such as the number of units included in each layer, information designating the type of a neuron that is a connection destination of each neuron, an activation function that realizes each neuron, and gates provided between units of the hidden layers. The activation function that realizes a neuron may be a function of switching operations according to input code (ReLU function or ELU function), a Sigmoid function, a step function, or a hyperbolic tangent function, or an identity function. A gate selectively passes or weights data transferred between units in response to a value (e.g., 1 or 0) returned according to the activation function, for example. The connection coefficient is a parameter of the activation function and includes a weight assigned to output data when the data is output from a neuron of a certain layer to a neuron of a deeper layer in a hidden layer of a neural network, for example. Further, the connection coefficient may include a unique bias component of each layer, and the like.

[Example of Configuration of Medical Image Reconstruction Model]

Figure 7:
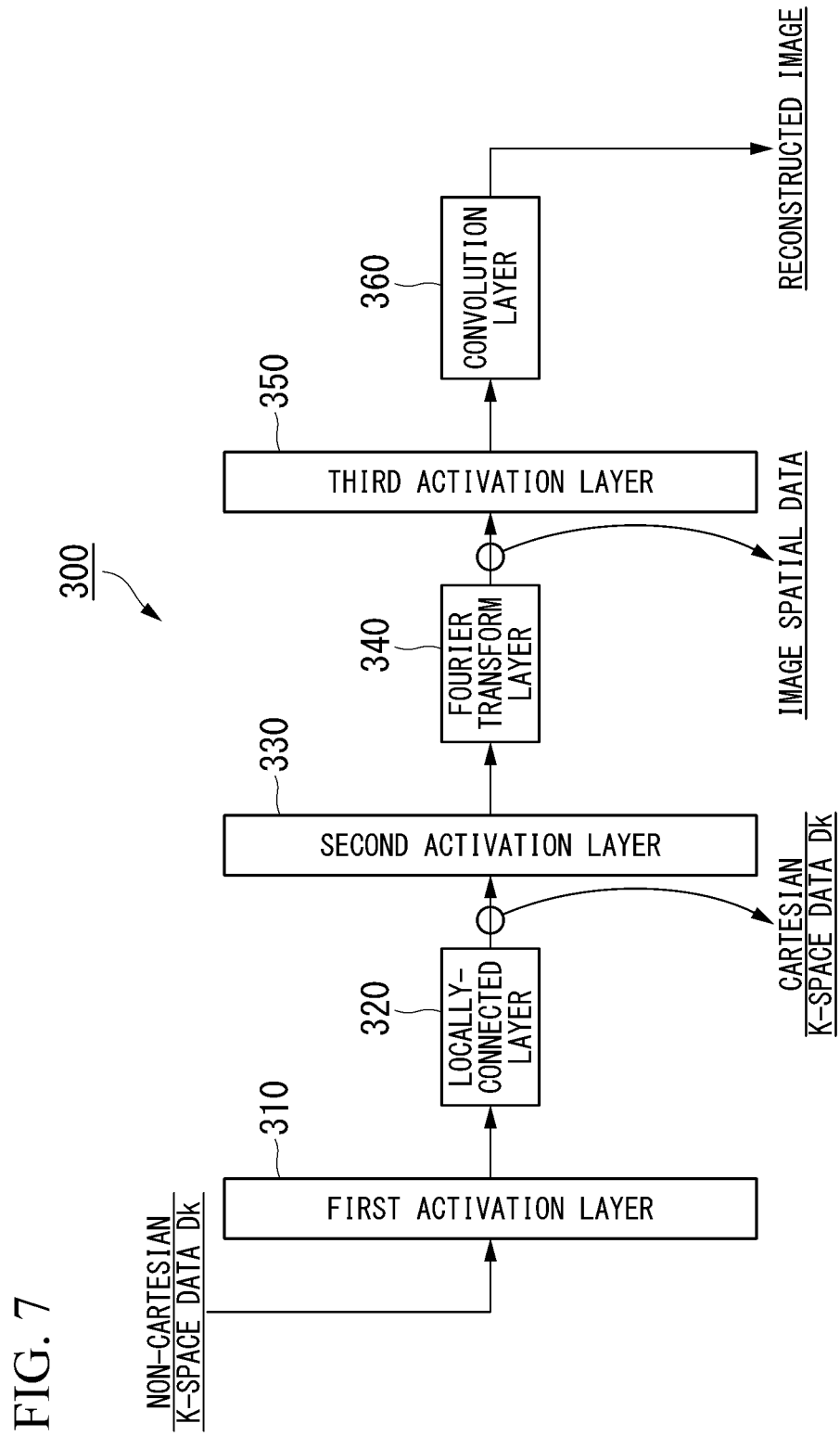
FIG. 7 is a diagram showing an example of a medical image reconstruction model according to the first embodiment.

FIG. 7 is a diagram showing an example of the medical image reconstruction model 300 in the first embodiment.

As shown, the medical image reconstruction model 300 may include a first activation layer 310, a locally-connected layer 320, a second activation layer 330, a Fourier transform layer 340, a third activation layer 350, and a convolution layer 360, for example.

The locally-connected layer 320 implemented as a function of the reconstruction processing function 214 is an example of a "first processor" and the Fourier transform layer 340 and the convolution layer 360 implemented as a function of the reconstruction processing function 214 are an example of a "second processor."

The vector representing the non-Cartesian k-space data Dk acquired through the acquisition function 212 is input to the first activation layer 310. For example, the first activation layer 310 may be implemented as a pooling layer, an activation function such as an ReLU function or Sigmoid function, or the like. When the first activation layer 310 includes a pooling layer, the first activation layer 310 compresses (reduces) the number of dimensions of the vector of the non-Cartesian k-space data Dk by exchanging element values of the vector of the non-Cartesian k-space data Dk with representative values such as average values or maximum values of all element values included in the vector. In addition, when the activation function of each node included in the first activation layer 310 is an ReLU function, for example, the first activation layer 310 sets each element value of the vector of the non-Cartesian k-space data Dk to zero when the element value is a negative value, and decreases the element value as the element value becomes closer to 0 and increases the element value as the element value becomes further from 0 when the element value is a positive value. Then, the first activation layer 310 outputs the vector on which pooling processing or activation function calculation processing has been performed to the locally-connected layer 320.

When the vector of the non-Cartesian k-space data Dk is input from the first activation layer 310, the locally-connected layer 320 multiplies the vector by a coefficient matrix L. The coefficient matrix L includes a plurality of coefficient sequences C represented by the product-sum coefficient information 234. A coefficient sequence C is a weight representing local characteristics and product-sum calculation thereof is performing calculation of $w_1x_1+w_2x_2+w_3x_3+\ldots$ on each output element. A parameter such as $x_1$, $x_2$ and $x_3$ represents an input and a parameter such as $w_1$, $w_2$ and $w_3$ represents a weight coefficient used in local product-sum calculation. In the coefficient matrix L, element values of elements other than local connection may be zero. The coefficient sequence C is an example of a "coefficient set."

Figures 8, 9:
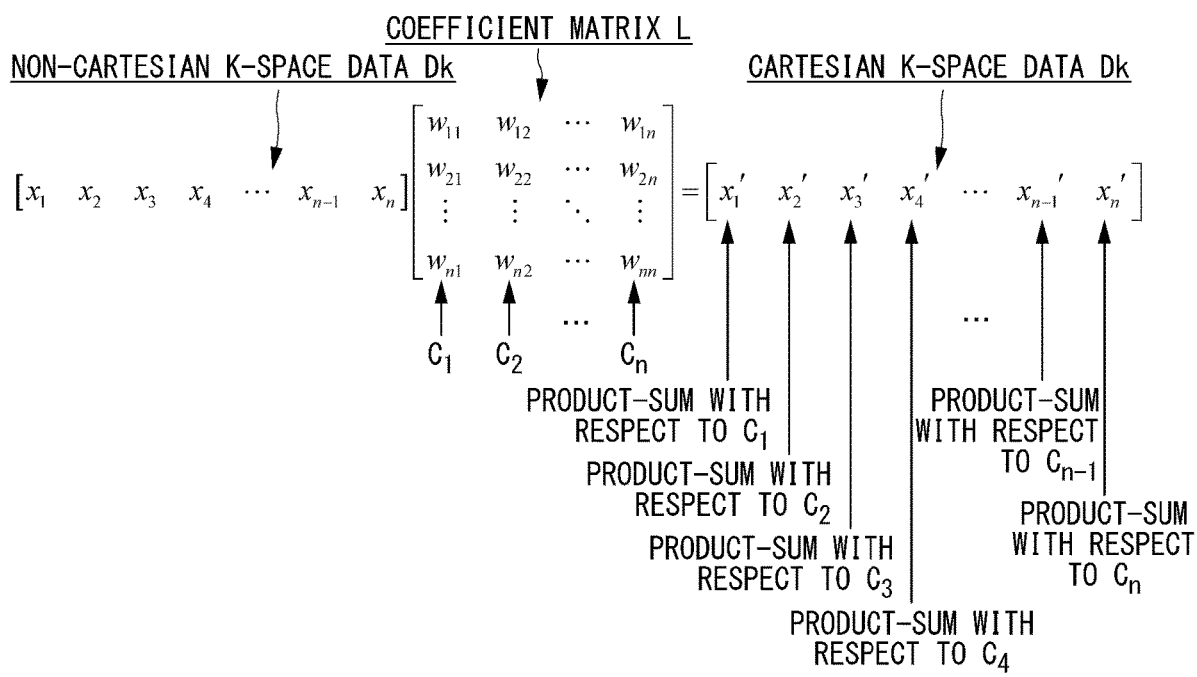
FIG. 8 is a diagram showing an example of product-sum coefficient information.
FIG. 9 is a diagram schematically showing a coefficient sequence and product-sum calculation.

FIG. 8 is a diagram showing an example of the product-sum coefficient information 234. As in the shown example, the product-sum coefficient information 234 is information in which a coefficient sequence C is associated with each assumed position of each sample point of the non-Cartesian k-space data Dk. An assumed position of a sample point may be a position logically obtained through a scanning method such as radial scan or spiral scan, a position obtained by performing correction (e.g., correction considering the influence of eddy current) based on imperfection of hardware on a logically obtained position, or a position statistically obtained from test data or simulation data.

Each of the plurality of coefficient sequences C included in the coefficient matrix L is determined by machine leaning for each assumed position of each sample point. Accordingly, the plurality of coefficient sequences C may become different coefficient sequences. Further, all of the plurality of coefficient sequences C need not be different and some thereof may be the same. For example, when a sample point and another sampling point are in a conjugate relation in the k space, coefficient sequences C associated with these sample points may be the same coefficient sequence. The conjugate relation is a relation in which sample points are point symmetrical or axial symmetrical in the k space, for example. Further, the coefficient sequence C may be configured to learn parameters of a parametric function determined in advance for each output position. For example, a Gaussian function may be employed as a parametric function and the coefficient sequence C may be caused to learn a Gaussian mixture. The Gaussian function may be another function such as a Kaiser window function.

FIG. 9 is a diagram schematically showing product-sum calculation of the coefficient sequence C. As in the shown example, the non-Cartesian k-space data Dk is represented by a vector including a plurality of elements corresponding to respective sample points such as $x_1, x_2, x_3, \ldots, x_{n-1}, x_n$ and the coefficient matrix L is represented by a matrix including a plurality of coefficient sequences such as $C_1, C_2, \ldots, C_{n-1}, C_n$. For example, the coefficient sequence $C_1$ is learned in advance using training data of a sample point $S_1$ which can be measured at an assumed position $P_1$ corresponding to the element $x_1$, and the coefficient sequence $C_2$ is learned in advance using training data of a sample point $S_2$ which can be measured at an assumed position $P_2$ corresponding to the element x2. The training data will be described later.

For example, the locally-connected layer 320 calculates products sums of element values x and coefficient sequences C included in the vector of the non-Cartesian k-space data Dk and generates a vector including a plurality of elements with which the sums of products are associated as element values as Cartesian k-space data Dk. The vector of the Cartesian k-space data Dk represents a vector in which sample points obtained by raster-scanning a two-dimensional image or a three-dimensional image are arranged in scan order.

As in the shown example, an element $x_1'$ included in the vector of the Cartesian k-space data Dk represents the product-sum of the element $x_1$ included in the vector of the non-Cartesian k-space data Dk and the coefficient sequence $C_1$ determined in advance according to machine learning, and an element x2' included in the vector of the Cartesian k-space data Dk represents the product-sum of the element $x_2$ included in the vector of the non-Cartesian k-space data Dk and the coefficient sequence $C_2$ determined in advance according to machine learning.

Although the number of elements of the coefficient sequence C is n that is the same as the number of elements (number of dimensions) of the vector of the non-Cartesian k-space data Dk, the present invention is not limited thereto and the number of elements of the coefficient sequence C may be a value less than n or greater than n.

When the Cartesian k-space data Dk is generated, the locally-connected layer 320 outputs the vector representing the Cartesian k-space data Dk to the second activation layer 330.

Referring back to FIG. 7, the vector of the Cartesian k-space data Dk is input to the second activation layer 330 from the locally-connected layer 320. Like the first activation layer 310, the second activation layer 330 may be implemented as a pooling layer, an activation function such as an ReLU function or Sigmoid function, or the like, for example. When the second activation layer 330 includes a pooling layer, the second activation layer 330 compresses the number of dimensions of the vector of the Cartesian k-space data Dk by exchanging element values of the vector of the Cartesian k-space data Dk with representative values such as average values or maximum values of all element values included in the vector. In addition, when the activation function of each node included in the second activation layer 330 is an ReLU function, for example, the second activation layer 330 sets each element value of the vector of the Cartesian k-space data Dk to zero when the element value is a negative value, and decreases the element value as the element value becomes closer to 0 and increases the element value as the element value becomes further from 0 when the element value is a positive value. Then, the second activation layer 330 outputs the vector of the Cartesian k-space data Dk on which pooling processing or activation function calculation processing has been performed to the Fourier transform layer 340.

The Fourier transform layer 340 performs a Fourier transform or an inverse Fourier transform on the vector of the Cartesian k-space data Dk input from the second activation layer 330. Input/output vectors of a Fourier transform may be or may not be consistent with the number of elements of a reconstructed output vector. For example, a Fourier transform may be applied with a number of elements 1.5 or 2 times the number of elements in each axial direction of a reconstructed image. The Fourier transform layer 340 outputs the Fourier transformed or inversely Fourier transformed vector of the Cartesian k-space data Dk to the third activation layer 350. The Fourier transformed or inversely Fourier transformed vector of the Cartesian k-space data Dk represents image spatial data in which pixel values are associated with physical position coordinates. In the following description, the Fourier transformed or inversely Fourier transformed vector of the Cartesian k-space data Dk is also referred to as image spatial data.

The Fourier transformed or inversely Fourier transformed vector, that is, the image spatial data, is input to the third activation layer 350 from the Fourier transform layer 340. Like the first activation layer 310 and the second activation layer 330, the third activation layer 350 may be implemented as a pooling layer, an activation function such as an ReLU function or Sigmoid function, or the like, for example. When the third activation layer 350 includes a pooling layer, the third activation layer 350 compresses the number of dimensions of the vector of the image spatial data by exchanging element values of the vector of the image spatial data with representative values such as average values or maximum values of all element values included in the vector. In addition, when the activation function of each node included in the third activation layer 350 is an ReLU function, for example, the third activation layer 350 sets each element value of the vector of the image spatial data to zero when the element value is a negative value, and decreases the element value as the element value becomes closer to 0 and increases the element value as the element value becomes further from 0 when the element value is a positive value. Then, the third activation layer 350 outputs the vector of the image spatial data on which pooling processing or activation function calculation processing has been performed to the convolution layer 360.

When the vector of the image spatial data is input from the third activation layer 350, the convolution layer 360 repeats product-sum calculation for the vector while sliding a linear transformation matrix (filter or kernel) with a certain determined stride amount and generates, from the vector of the input image spatial data, a vector including a plurality of elements with which product-sums with respect to the linear transformation matrix are associated as element values. Then, the convolution layer 360 outputs data of the generated vector as a reconstructed image of the medial image (MR image).

The output control function 216 outputs the reconstructed image output from the convolution layer 360 to the medical image generation apparatus 100 connected through the communication interface 202, for example. Further, the output control function 216 may cause the display 206 to output (display) the reconstructed image.

[Processing Flow]

Figure 10:
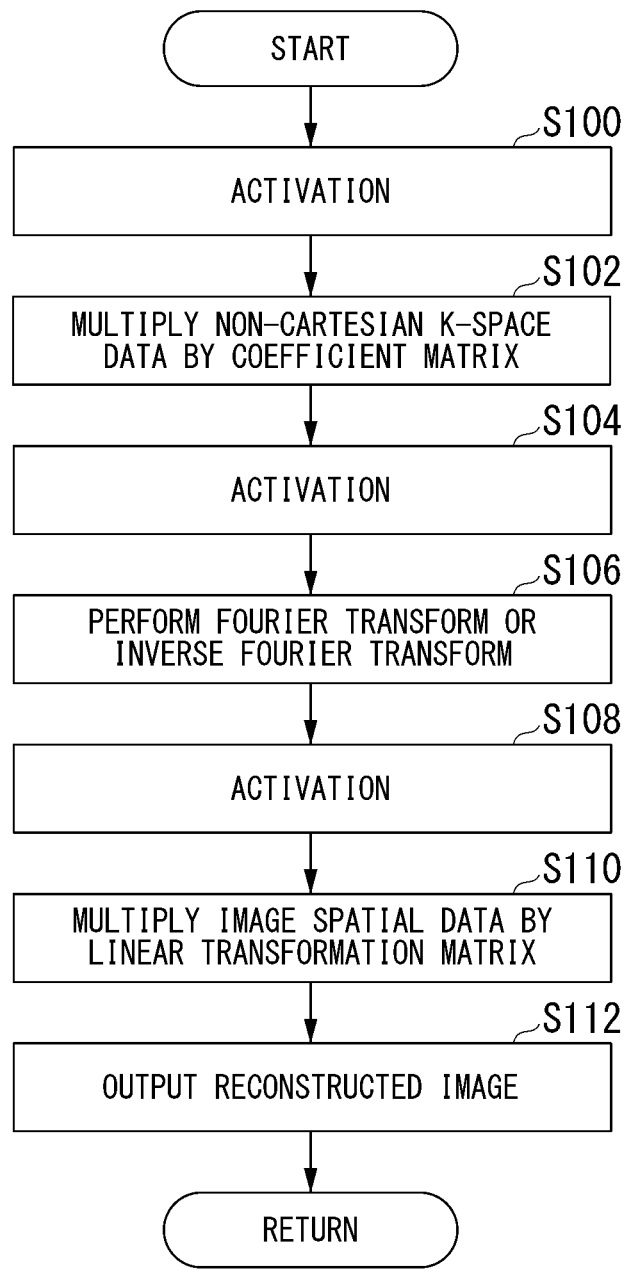
FIG. 10 is a flowchart showing a flow of a series of processes of a processing circuit in the present embodiment.

Hereinafter, a flow of a series of processes of the processing circuit 210 in the present embodiment will be described based on a flowchart. FIG. 10 is a flowchart showing a flow of a series of processes of the processing circuit 210 in the present embodiment. The processes of this flowchart may be repeatedly performed at a predetermined period when non-Cartesian k-space data Dk has been acquired through the acquisition function 212.

First, the first activation layer 310 performs activation such as pooling processing or activation function calculation processing on the vector of the non-Cartesian k-space data Dk acquired through the acquisition function 212 (step S100).

Next, the locally-connected layer 320 multiplies the vector on which pooling processing, activation function calculation processing or the like has been performed by the first activation layer 310 by the coefficient matrix L (step S102). Specifically, the locally-connected layer 320 calculates product-sums of a coefficient sequence C corresponding to the positions of sample points (elements of the vector) in the k space and elements of the vector and generates a vector including a plurality of elements with which the products sums are associated as element values as Cartesian k-space data Dk.

Next, the second activation layer 330 performs activation such as pooling processing or activation function calculation processing on the vector of the Cartesian k-space data Dk generated by the locally-connected layer 320 (step S104).

Next, the Fourier transform layer 340 performs a Fourier transform or an inverse Fourier transform on the vector on which pooling processing, activation function calculation processing or the like has been performed by the second activation layer 330 (step S106). Accordingly, image spatial data is generated.

Next, the third activation layer 350 performs activation such as pooling processing or activation function calculation processing on the vector of the image spatial data generated by the Fourier transform layer 340 (step S108).

Next, the convolution layer 360 calculates product-sums of the vector of the image spatial data on which pooling processing, activation function calculation processing or the like has been performed by the third activation layer 350 and a linear transformation matrix (step S110). Specifically, the convolution layer 360 generates a vector including a plurality of elements with which product-sums with respect to the linear transformation matrix are associated as element values from the vector of the image spatial data by repeating product-sum calculation while sliding the linear transformation matrix with a certain determined slide amount. Then, the convolution layer 360 outputs data of the generated vector as a reconstructed image of a medical image.

Next, the output control function 216 causes the display 206 to display the reconstructed image of the medical image output from the convolution layer 360 or transmits the reconstructed image to the medical image generation apparatus 100 through the communication interface 202 (step S112). Accordingly, the processes of this flowchart end.

[Method of Learning Medical Image Reconstruction Model]

Hereinafter, a method of learning the medical image reconstruction model 300 will be described. The learning function 218 causes the medical image reconstruction model 300 to be learned basis on certain training data. For example, the training data may be data for which non-Cartesian k-space data Dk having a greater number of samples when scanned than in a normal case has been prepared, and having a subset of the non-Cartesian k-space data Dk as input and having a reconstructed image obtained by reconstructing the non-Cartesian k-space data Dk through a known technique as output. Further, data obtained by performing a sampling simulation on any medical image to acquire non-Cartesian k-space data Dk and associating a medical image with the acquired non-Cartesian k-space data Dk as correct-answer data may be used as the training data.

The learning function 218 inputs certain non-Cartesian k-space data Dk to the first activation layer 310 of the medical image reconstruction model 300 and causes parameters of an activation function of each node of the first activation layer 310, the second activation layer 330 and the third activation layer 350, each coefficient sequence C included in the coefficient matrix L of the locally-connected layer 320, and parameters of a linear transformation matrix of the convolution layer 360 to be learned such that a reconstructed image obtained by using functions to be learned (functions of realizing all layers from 310 to 360 in the example of FIG. 7) becomes close to the reconstructed image which is the training data. For example, the learning function 218 may cause the parameters to be learned using gradient methods such as Stochastic Gradient Descent (SGD), momentum SGD, AdaGrad, RMSprop, AdaDelta, and Adaptive moment estimation (Adam).

According to the above-described first embodiment, it is possible to improve the accuracy of reconstruction of an MR image that is one of medical images to generate a medical image with high picture quality through reconstruction by including the acquisition function 212 which acquires non-Cartesian k-space data Dk generated by applying magnetic fields to the test object OB from the medical image generation apparatus 100, the locally-connected layer 320 which derives product-sums of the acquired non-Cartesian k-space data Dk and a plurality of coefficient sequences C and generates a vector including a plurality of elements with which the product-sums derived for the coefficient sequences C are associated as element values as Cartesian k-space data Dk, the Fourier transform layer 340 which performs a Fourier transform or an inverse Fourier transform on the generated Cartesian k-space data Dk, and the convolution layer 360 which generates an image including a plurality of pixels with which product-sums obtained by multiplying the Fourier transformed or inversely Fourier transformed Cartesian k-space data Dk by a linear connection matrix are associated as pixel values as a reconstructed image of an MR image.

Modified Example of First Embodiment

Hereinafter, a modified example of the first embodiment will be described. Although the medical image generation apparatus 100 and the medical image processing apparatus 200 are different apparatuses in the above-described first embodiment, the present invention is not limited thereto. For example, the medical image processing apparatus 200 may be implemented as a function of the console device 120 of the medical image generation apparatus 100. That is, the medical image processing apparatus 200 may be a virtual machine virtually implemented as the console device 120 of the medical image generation apparatus 100.

Figure 11:
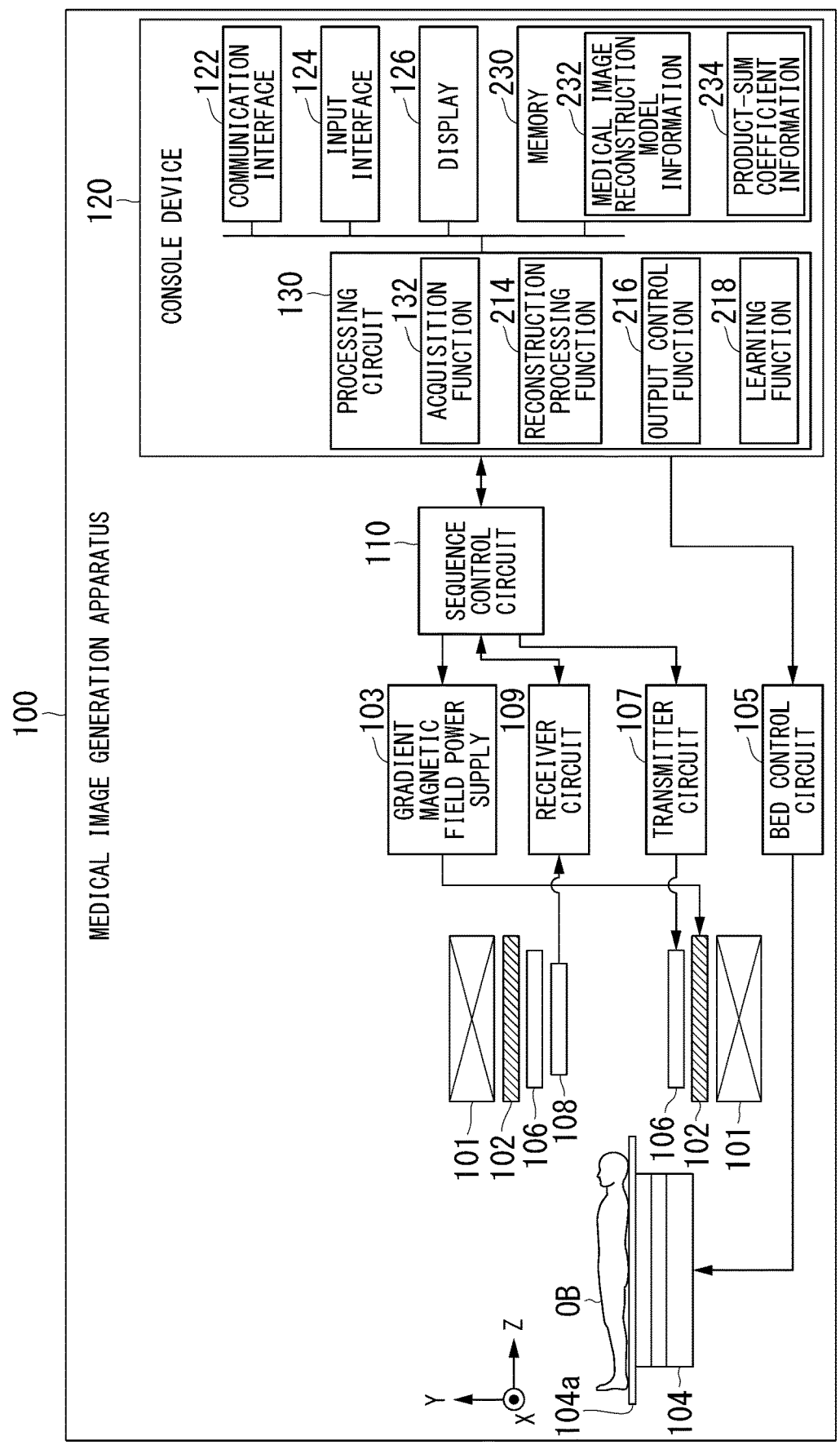
FIG. 11 is a diagram showing another example of the medical image generation apparatus according to the first embodiment.

FIG. 11 is a diagram showing another example of the medical image generation apparatus 100 according to the first embodiment. As shown in FIG. 11, the processing circuit 130 of the console device 120 may execute the reconstruction processing function 214, the output control function 216 and the learning function 218 in addition to the above-described acquisition function 132.

In addition, the medical image reconstruction model information 232 and the product-sum coefficient information 234 may be stored in the memory 150 of the console device 120.

According to such a configuration, it is possible to generate a medical image with high picture quality through reconfiguration using the medical image generation apparatus 100 alone.

In addition, although the locally-connected layer 320 generates one vector in the above-described first embodiment, the present invention is not limited thereto. For example, when the medical image generation apparatus 100 simultaneously collects a plurality of pieces of k-space data Dk through multiple coils, the locally-controlled layer 320 may generate a plurality of vectors corresponding to the respective coils. When the locally-connected layer 320 generates a plurality of vectors, that is, in the case of multiple channels, the medical image reconstruction model 300 following the locally-connected layer 320 may be configured as multiple stages for the channels.

Further, when the medical image generation apparatus 100 simultaneously collects a plurality of pieces of k-space data Dk through multiple coils in the above-described first embodiment, the reconstruction processing function 214 may increase the number of samples of k-space data which is input data for the medical image reconstruction model 300 basis on information of the multiple coils (a plurality of pieces of coil information).

Further, although the locally-connected layer 320 calculates a product-sum of input data and the coefficient sequence C through convolution in the above-described first embodiment, the present invention is not limited thereto. For example, the locally-connected layer 320 may calculate a product-sum of input data and a parametric window function through convolution. A parameter of the parametric window function associated with each input or each output is learned by the learning function 218 like other parameters constituting a deep neural network.

In addition, the third activation layer 350 and the convolution layer 360 are provided after the Fourier transform layer 340 in the medical image reconstruction model 300 in the above-described first embodiment, the present invention is not limited thereto. For example, an image transformation layer may be provided after the convolution layer 360 in the medical image reconstruction model 300. For example, the image transformation layer performs transformation processing such as extension, contraction and rotation on a reconstructed image output from the convolution layer 360.

Further, other activation layers and other convolution layers may be provided after the convolution layer 360 in the medical image reconstruction model 300. That is, convolution layers may be configured as multiple stages in the medical image reconstruction model 300.

Although an activation layer is not provided in principle further after a convolution layer in the latest stage in the above-described first embodiment and the modified example thereof, the present invention is not limited thereto and any activation layer may be provided after the convolution layer in the latest stage.

In addition, the locally-connected layer 320 (an example of the first processor) may convert Cartesian k-space data Dk into non-Cartesian k-space data by mixing generated Cartesian k-space data Dk with one or more dummy sample points in the above-described first embodiment. Further, other layers such as the Fourier transform layer 340 may convert Cartesian k-space data Dk into non-Cartesian k-space data by mixing Cartesian k-space data Dk generated by the locally-connected layer 320 with one or more dummy sample points.

Second Embodiment

Hereinafter, the second embodiment will be described. The medical image reconstruction model 300 includes one locally-connected layer 320 in the first embodiment. In contrast, the second embodiment differs from the above-described first embodiment in that the medical image reconstruction model 300 includes two or more locally-connected layers. Hereinafter, the description will focus on differences from the first embodiment and a description of common points of the first and second embodiment will be omitted. Further, in the description of the second embodiment, the same reference numbers will be used to refer to the same parts as those in the first embodiment.

Figure 12:
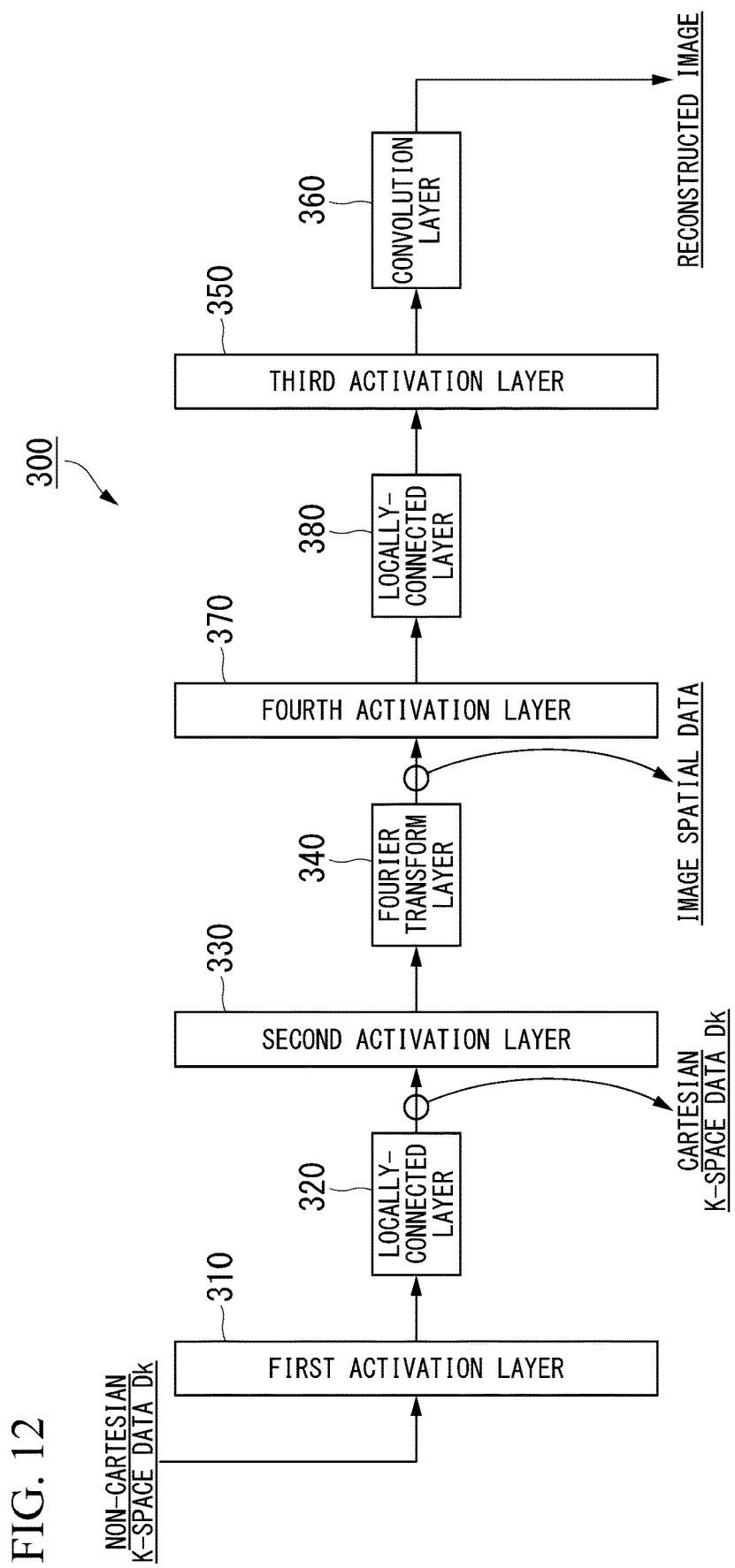
FIG. 12 is a diagram showing an example of a medical image reconstruction model according to a second embodiment.

FIG. 12 is a diagram showing an example of the medical image reconstruction model 300 in the second embodiment. As shown, the medical image reconstruction model 300 in the second embodiment includes, for example, the first activation layer 310, the locally-connected layer (first locally-connected layer) 320, the second activation layer 330, the Fourier transform layer 340, the third activation layer 350 and the convolution layer 360 like the medical image reconstruction model 300 in the first embodiment and further includes a fourth activation layer 370 and a second locally-connected layer 380. The fourth activation layer 370 and the second locally-connected layer 380 are provided between the Fourier transform layer 340 and the third activation layer 350. A combination of the Fourier transform layer 340, the second locally-connected layer 380 and the convolution layer 360 is another example of the "second processor."

A Fourier transformed or inversely Fourier transformed vector, that is, image spatial data is input to the fourth activation layer 370 from the Fourier transform layer 340. Like the first activation layer 310 and the second activation layer 330, the fourth activation layer 370 may be implemented as a pooling layer, an activation function or the like, for example. The fourth activation layer 370 performs a pooling processing or activation function calculation processing on the vector of the input image spatial data and outputs the resultant vector to the second locally-connected layer 380.

When the vector of the image spatial data is input from the fourth activation layer 370, the second locally-connected layer 380 multiplies the vector by a coefficient matrix L including a plurality of coefficient sequences C. Specifically, the second locally-connected layer 380 calculates a product-sum of each element of the vector of the image spatial data and each coefficient sequence C and generates a vector including a plurality of elements with which the product-sums are associated as element values. The second locally-connected layer 380 outputs the generated vector to the third activation layer 350. Accordingly, a medical image with high picture quality can be generated through reconstruction as in the first embodiment.

Further, the fourth activation layer 370 and the second locally-connected layer 380 may be provided at other positions instead of being provided between the Fourier transform layer 340 and the third activation layer 350.

Figure 13:
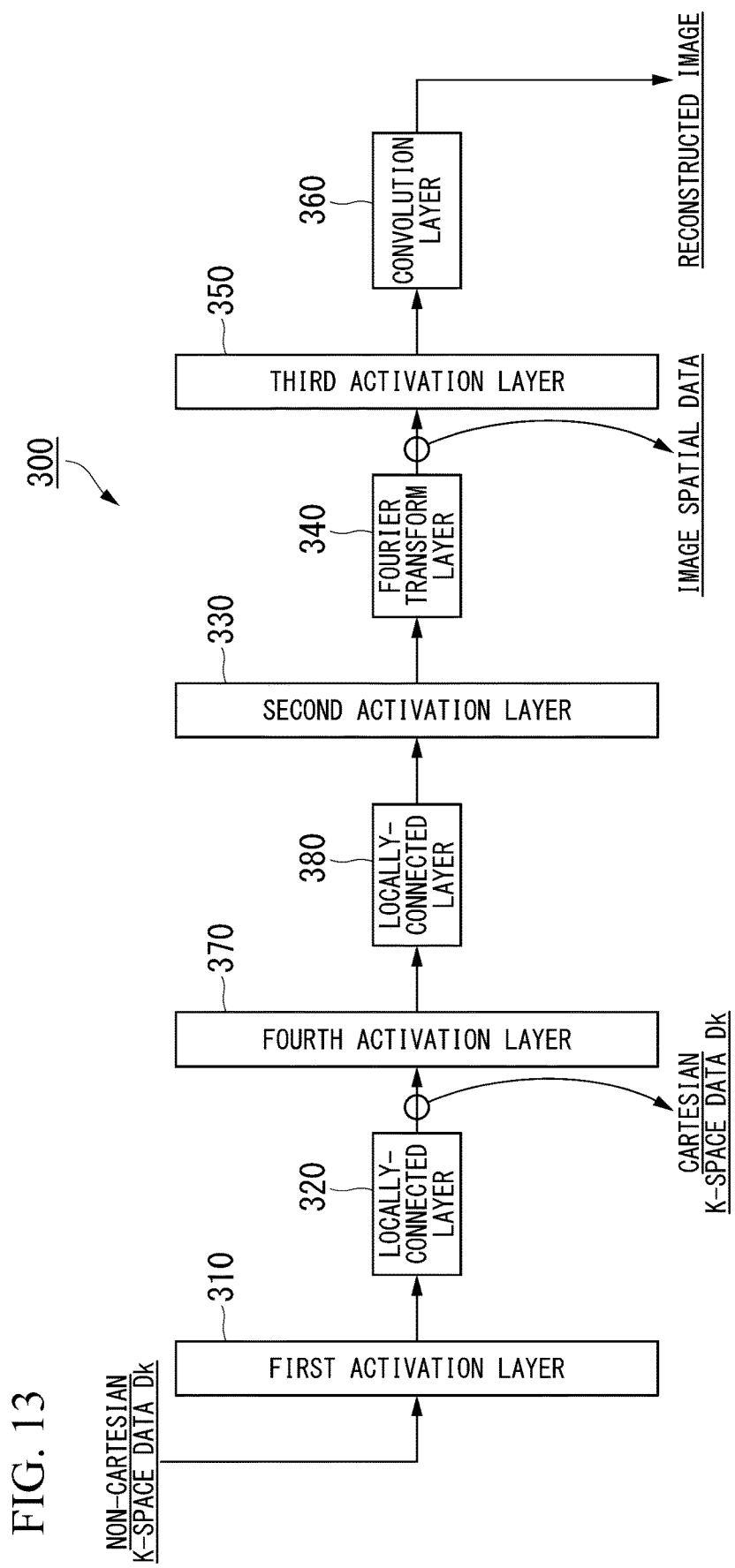
FIG. 13 is a diagram showing another example of the medical image reconstruction model according to the second embodiment.

FIG. 13 is a diagram showing another example of the medical image reconstruction model 300 in the second embodiment. As shown, the fourth activation layer 370 and the second locally-connected layer 380 may be provided between the locally-connected layer 320 and the Fourier transform layer 340. In this manner, it is possible to mitigate nonlinearity of non-Cartesian k-space data Dk which can be generated due to imaging of the test object OB through radial scan or spiral scan by providing the second locally-connected layer 380 before the Fourier transform layer 340 in the second embodiment.

Figure 14:
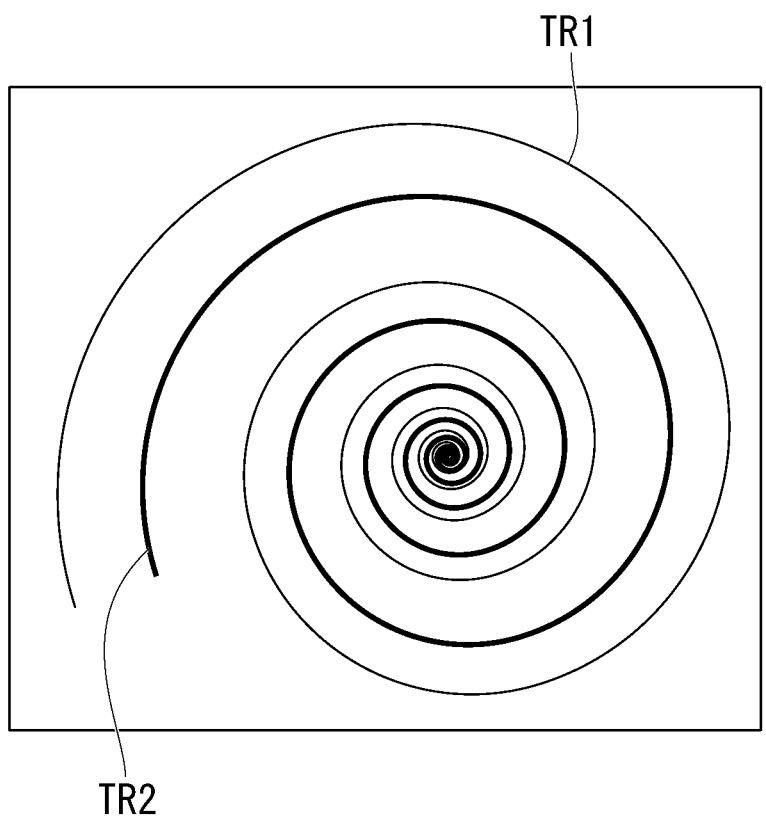
FIG. 14 is a diagram showing nonlinearity of non-Cartesian k spatial data.

FIG. 14 is a diagram showing nonlinearity of non-Cartesian k-space data Dk.

In the figure, TR1 and TR2 represent trajectories connecting sample points included in the non-Cartesian k-space data Dk in scan order. The trajectory TR1 represents an ideal trajectory and the trajectory TR2 represents an actually measured trajectory.

For example, when the actually measured trajectory TR2 is distorted, a signal is attenuated or the test object OB is moved, there is a case in which the actually measured trajectory TR2 deviates from the ideal trajectory TR1. In this case, when the coefficient sequence C handled by each locally-connected layer is designed at the position of each sample point on the ideal trajectory TR1, the actually measured trajectory TR2 deviates from reference sampling points for design of the coefficient sequence C, and thus an output result of the locally-connected layer includes an error.

In contrast, since the second locally-connected layer 380 is provided before the Fourier transform layer 340 in the second embodiment, the learning function 218 can learn the coefficient sequence C of the second locally-connected layer 380 to correct non-Cartesian k-space data Dk such that a deviation of the actually measured trajectory TR2 from the original trajectory (trajectory TR1 referred to when the coefficient sequence C is designed) is eliminated.

Although the second locally-connected layer 380 is provided before or after the Fourier transform layer 340 in the second embodiment, the present invention is not limited thereto and an activation layer and a locally-connected layer may be provided, for example, before the Fourier transform layer 340 (between the locally-connected layer 320 and the Fourier transform layer 340) and after the Fourier transform layer 340 (between the Fourier transform layer 340 and the convolution layer 360).

According to the above-describe second embodiment, it is possible to generate a medical image with high picture quality through reconstruction by providing two or more locally-connected layer to the medical image reconstruction model 300 as in the first embodiment. Particularly when the second locally-connected layer 380 is provided before the Fourier transform layer 340, it is possible to generate a medical image with higher picture quality through reconstruction because nonlinearity of non-Cartesian k-space data Dk can be mitigated.

Third Embodiment

Hereinafter, the third embodiment will be described. The third embodiment differs from the above-described first and second embodiments in that processing suitable for the number of sample points assumed when the medical image reconstruction model 300 is learned is performed on non-Cartesian k-space data Dk having a different total number of sample points as pre-processing. Hereinafter, the description will focus on differences from the first and second embodiments and a description of common points of the first, second and third embodiments will be omitted. Further, in the description of the third embodiment, the same reference numbers will be used to refer to the same parts as those in the first and second embodiments.

Figure 15:
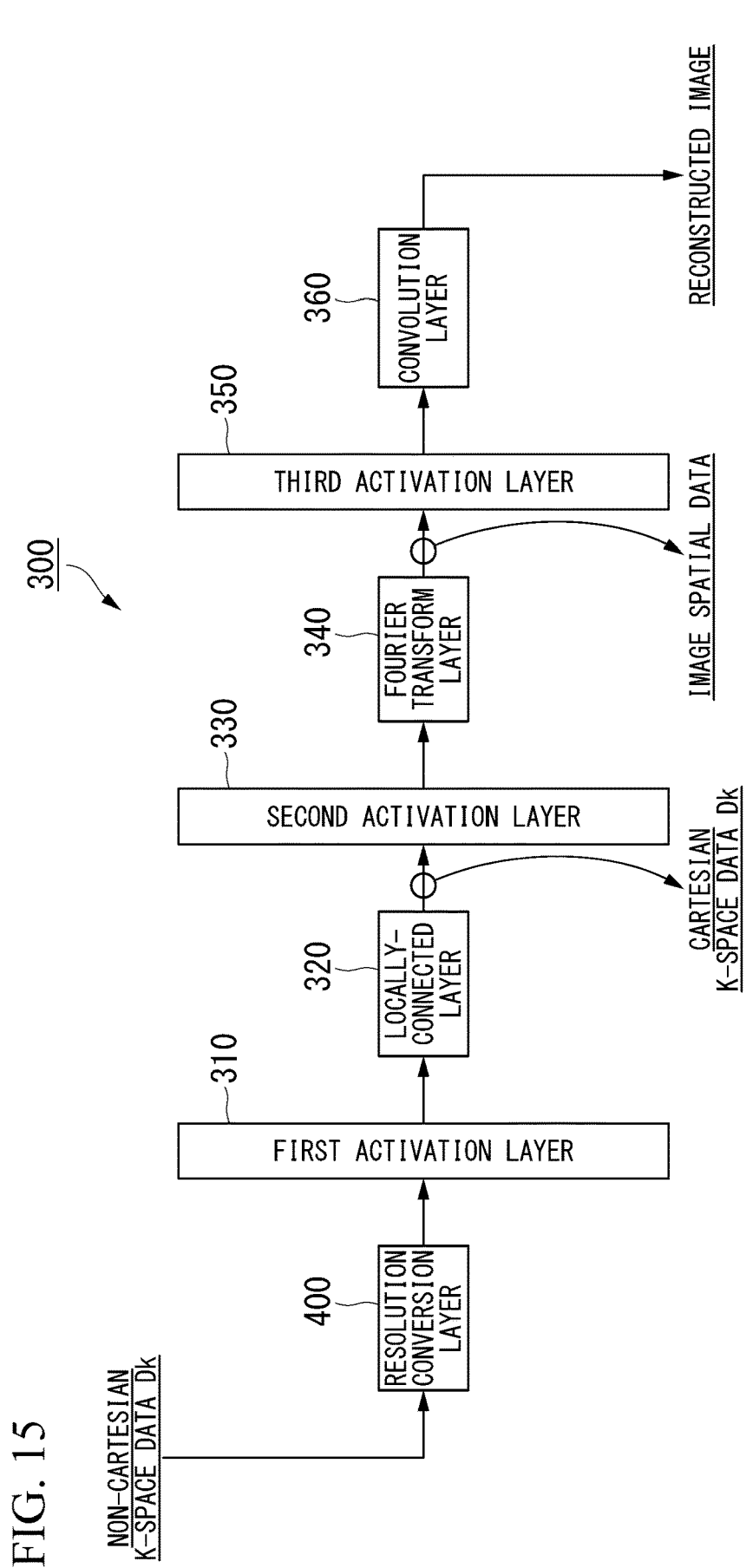
FIG. 15 is a diagram showing an example of a medical image reconstruction model according to a third embodiment.

FIG. 15 is a diagram showing an example of the medical image reconstruction model 300 in the third embodiment. As shown, the medical image reconstruction model 300 in the third embodiment includes, for example, the first activation layer 310, the locally-connected layer (first locally-connected layer) 320, the second activation layer 330, the Fourier transform layer 340, the third activation layer 350 and the convolution layer 360 like the medical image reconstruction model 300 in the first embodiment and further includes a resolution conversion layer 400. The resolution conversion layer 400 is provided before the locally-controlled layer 320. The resolution conversion layer 400 implemented as a function of the reconstruction processing function 214 is an example of a "third processor."

The resolution conversion layer 400 provided for pre-processing may be implemented, for example, by a certain locally-connected layer. A vector indicating non-Cartesian k-space data Dk acquired through the acquisition function 212 is input to the resolution conversion layer 400. Here, the number of rows and the number of columns of the non-Cartesian k-space data Dk need not be set to one and may be different whenever the non-Cartesian k-space data Dk is acquired through the acquisition function 212.

When the vector of the non-Cartesian k-space data Dk acquired through the acquisition function 212 is input, the resolution conversion layer 400 generates non-Cartesian k-space data Dk having the same number of elements (dimensions) as that of non-Cartesian k-space data Dk assumed when the medical image reconstruction model 300 is learned by multiplying the vector by a linear transformation matrix. The resolution conversion layer 400 outputs the generated vector of the non-Cartesian k-space data Dk to the first activation layer 310.

According to the above-described third embodiment, it is possible to generate a medical image with high picture quality through reconstruction even when a medical image has a multi-resolution and non-Cartesian k-space data Dk having a different number of sample points is input to the medical image reconstruction model 300 by providing the resolution conversion layer 400 in the forefront of the medical image reconstruction model 300.

Modified Example of Third Embodiment

Hereinafter, a modified example of the third embodiment will be described. Although a medical image is generated through reconstruction even when a medical image has a multi-resolution by providing the resolution conversion layer 400 in the forefront of the medical image reconstruction model 300 in the above-described third embodiment, the present invention is not limited thereto. For example, a plurality of resolution conversion layers 400 may be connected in series to the forefront of the medical image reconstruction model 300. Further, a layer or DNN performing linear interpolation or a layer or DNN performing zero fill instead of the resolution conversion layer 400 may be provided in the forefront of the medical image reconstruction model 300. The layer or DNN performing linear interpolation performs processing of supplementing insufficient sampling points with other sample points through linear interpolation, for example, when the number of sample points included in non-Cartesian k-space data Dk is small and the non-Cartesian k-space data Dk has a low resolution. The layer or DNN performing zero fill performs processing of supplementing insufficient sample points with elements having an element value of zero when the number of sample points included in non-Cartesian k-space data Dk is small and the non-Cartesian k-space data Dk has a low resolution.

It is possible to arrange the number of sample points included in non-Cartesian k-space data Dk by providing a plurality of resolution conversion layers 400 in the forefront of the medical image reconstruction model 300, providing a layer or DNN performing linear interpolation therein or providing a layer or DNN performing zero fill therein, as described above.

Fourth Embodiment

Hereinafter, the fourth embodiment will be described. The medical image generation apparatus 100 is an MRI apparatus in the above-described first to third embodiments. In contrast, the fourth embodiment differs from the above-described first to third embodiments in that the medical image generation apparatus 100 is a CT apparatus. Hereinafter, the description will focus on differences from the first to third embodiments and a description of common points of the first to third embodiments will be omitted. Further, in the description of the fourth embodiment, the same reference numbers will be used to refer to the same parts as those in the first to third embodiments.

[Example of Configuration of Medical Image Generation Apparatus (X-Ray CT Apparatus)]

Figure 16:
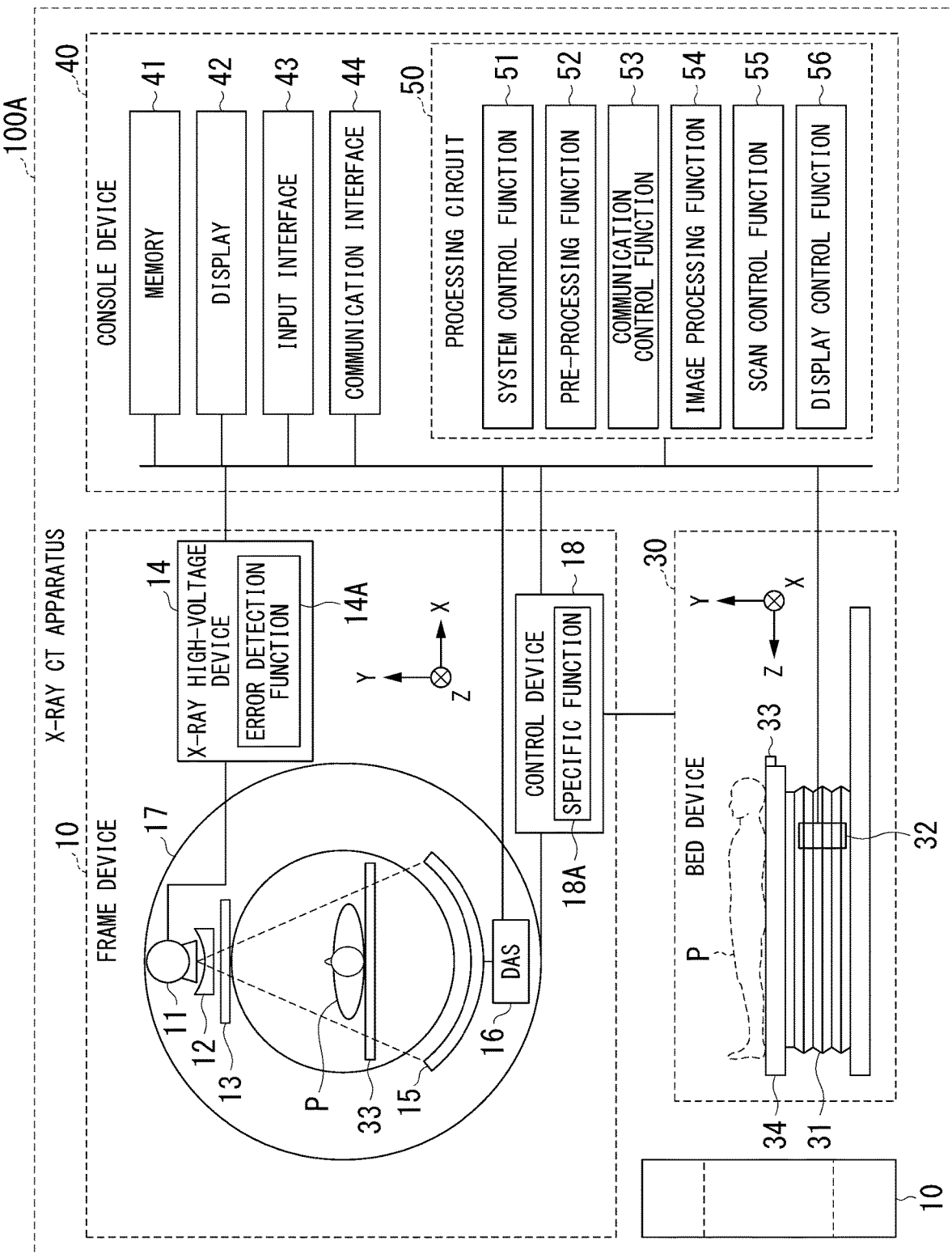
FIG. 16 is a diagram showing an example of a medical image generation apparatus according to a fourth embodiment.

FIG. 16 is a diagram showing an example of a medical image generation apparatus 100A according to the fourth embodiment. As shown in FIG. 16, the medical image generation apparatus 100A includes a frame device 10, a bed device 30, and a console device 40, for example. Although FIG. 16 shows both a diagram of the frame device 10 viewed in the Z-axis direction and a diagram thereof viewed in the X-axis direction for convenience of explanation, there is actually one frame device 10. In an embodiment, the longitudinal direction of a rotation axis of a rotating frame 17 in a non-tilt state or a top board 33 of the bed device 30 is defined as the Z-axis direction, an axis orthogonal to the Z-axis direction and parallel to the floor face is defined as the X-axis direction, and a direction orthogonal to the Z-axis direction and perpendicular to the floor face is defined as the Y-axis direction.

For example, the frame device 10 includes an X-ray tube 11, a wedge 12, a collimator 13, an X-ray high-voltage device 14, an X-ray detector 15, a data collection system (hereinafter, data acquisition system (DAS)) 16, a rotating frame 17, and a control device 18.

The X-ray tube 11 generates X-rays (radioactive rays) by radiating thermions from a cathode (filament) to an anode (target) according to application of a high voltage from the X-ray high-voltage device 14.

The X-ray tube 11 includes a vacuum tube. For example, the X-ray tube 11 is a rotating anode X-ray tube that generates X-rays by radiating thermions to a rotating anode.

The wedge 12 is a filter for controlling an X-ray dose radiated to a test object P from the X-ray tube 11. The wedge 12 attenuates X-rays transmitting the wedge 12 such that a distribution of the X-ray dose radiated to the test object P from the X-ray tube 11 becomes a predetermined distribution. The wedge 12 is also called a wedge filter or a bow-tie filter. For example, the wedge 12 is implemented as processing aluminum such that it has a predetermined target angle and a predetermined thickness.

The collimator 13 is a mechanism for narrowing a radiation range of X-rays that has transmitted the wedge 12. The collimator 13 narrows the X-ray radiation range, for example, by forming a slit using a combination of a plurality of lead plates. The collimator 13 may also be called an X-ray aperture.

The X-ray high-voltage device 14 includes a high-voltage generation device and an X-ray control device, for example. The high-voltage generation device includes an electrical circuit including a transformer and a rectifier and generates a high voltage to be applied to the X-ray tube 11. The X-ray control device controls an output voltage of the high-voltage generation device depending on an X-ray dose to be generated by the X-ray tube 11. The high-voltage generation device may perform voltage boosting using the aforementioned transformer or perform voltage boosting using an inverter.

The X-ray high-voltage device 14 may be provided in the rotating frame 17 or provided on the side of a fixed frame (not shown) of the frame device 10. Further, the X-ray high-voltage device 14 includes an error detection function 14A. This will be described later.

The X-ray detector 15 detects the intensity of X-rays that are generated by the X-ray tube 11, pass through the test object P and are input thereto. The X-ray detector 15 outputs an electrical signal (an operation signal or the like) in response to the detected intensity of X-rays to the DAS 18. The X-ray detector 15 includes a plurality of X-ray detection element sequences, for example. The plurality of X-ray detection element sequences are arrangement of a plurality of X-ray detection elements in a channel direction along an arc having the focal point of the X-ray tube 11 as a center. The plurality of X-ray detection element sequences are arranged in a slice direction (column direction, row direction).

The X-ray detector 15 is an indirect type detector having a grid, a scintillator array and an optical sensor array. The scintillator array has a plurality of scintillators. Each scintillator has scintillator crystals. The scintillator crystals emits a quantity of light depending on the intensity of incident X-rays. The grid is disposed on the face of the scintillator array on which X-rays are incident and includes an X-ray shielding plate having a function of absorbing scattering X-rays. Further, the grid may also be called a collimator (one-dimensional collimator or two-dimensional collimator). The optical sensor array includes optical sensors such as photomultiplier tubes (PMTs) or the like, for example. The optical sensor array outputs an electrical signal depending on the quantity of light emitted from the scintillators. The X-ray detector 15 may be a direct conversion type detector having a semiconductor element which converts incident X-rays into an electrical signal.

The DAS 16 includes an amplifier, an integrator and an A/D converter, for example. The amplifier performs amplification processing on an electrical signal output from each X-ray detection element of the X-ray detector 15. The integrator integrates the electrical signal on which amplification processing has been performed over a view period (which will be described later). The A/D converter converts an electrical signal indicating an integration result into a digital signal. The DAS 16 outputs detected data based on the digital signal to the console device 40. The detected data is a digital value of X-ray intensity identified by a channel number and a column number of an X-ray detection element that is a generation source, and a view number indicating a collected view. The view number is a number varying according to rotation of the rotating frame 17 and, for example, a number incremented according to rotation of the rotating frame 17. Accordingly, the view number is information indicating a rotation angle of the X-ray tube 11. A view period is a period falling between a rotation angle corresponding to a certain view number and a rotation angle corresponding to the next view number. The DAS 16 may detect view switching according to a timing signal input from the control device 18, detect it using an internal timer, or detect it according to a signal acquired from a sensor which is not shown. When X-rays are continuously exposed by the X-ray tube 11 in a case in which full scan is performed, the DAS 16 collects detected data groups of the entire circumference (360 degrees). When X-rays are continuously exposed by the X-ray tube 11 in a case in which half scan is performed, the DAS 16 collects detected data of half circumference (180 degrees).

The rotating frame 17 is an annular member which supports the X-ray tube 11, the wedge 12, the collimator 13 and the X-ray detector 15 such that the X-ray tube 11, the wedge 12 and the collimator 13 face the X-ray detector 15. The rotating frame 17 is rotatably supported by a fixed frame having the test object P introduced into the inside thereof as the center. The rotating frame 17 further supports the DAS 16. Detected data output from the DAS 16 is transmitted from a transmitter having a light-emitting diode (LED) provided in the rotating frame 17 to a receiver having a photo diode provided in a non-rotating part (e.g., the fixed frame) of the frame device 10 and forwarded by the receiver to the console device 40. A method of transmitting detected data from the rotating frame 17 to the non-rotating part is not limited to the above-described method using optical communication and may employ any contactless transmission method. The rotating frame 17 is not limited to an annular member and may be a member such as an arm if it can support and rotate the X-ray tube 11 or the like.

Although the medical image generation apparatus 100A that is an X-ray CT apparatus is, for example, a rotate/rotate-type X-ray CT apparatus (third-generation CT) in which both the X-ray tube 11 and the X-ray detector 15 are supported by the rotating frame 17 and rotate around the test object P, the medical image generation apparatus 100A is not limited thereto and may be a stationary/rotate-type X-ray CT apparatus (fourth-generation CT) in which a plurality of X-ray detection elements arranged in an annular form are fixed to a fixing frame and the X-ray tube 11 rotates around the test object P.

The control device 18 includes a processing circuit having a processor such as a CPU, and a driving mechanism including a motor, an actuator and the like, for example. The control device 18 receives an input signal from an input interface 43 attached to the console device 40 or the frame device 10 and controls operations of the frame device 10 and the bed device 30. For example, the control device 18 rotates the rotating frame 17, tilts the bed device 10 or moves the top board 33 of the bed device 30. When the control device 18 tilts the frame device 10, the control device 18 rotates the rotating frame 17 on an axis parallel to the Z-axis direction basis on an inclination angle (tilt angle) input to the input interface 43. The control device 18 ascertains a rotation angle of the rotating frame 17 through an output of a sensor which is not shown, or the like. In addition, the control device 18 provides the rotation angle of the rotating frame 17 to a scan control function 55 at any time. The control device 18 may be provided in the frame device 10 or in the console device 40. Further, the processing circuit of the control device 18 includes a specific function 18A. This will be described later.

The bed device 30 is a device which moves the test object P that is a scan target and is mounted thereon and introduces the test object P into the inside of the rotating frame 17 of the frame device 10. The bed device 30 includes a base 31, a bed driving device 32, the top board 33, and a support frame 34, for example. The base 31 includes a housing which supports the support frame 34 such that the support frame 34 can be moved in a vertical direction (Y-axis direction). The bed driving device 32 includes a motor and an actuator. The bed driving device 32 moves the top board 33 on which the test object P is mounted in the longitudinal direction (Z-axis direction) of the top board 33 along the support frame 34. The top board 33 is a plate-shaped member on which the test object P is mounted.

The bed driving device 32 may move not only the top board 33 but also the support frame 34 in the longitudinal direction of the top board 33. On the contrary, the frame device 10 is movable in the Z-axis direction and the rotating frame 17 may be controlled such that it comes to the test object P according to movement of the frame device 10. Further, both the frame device 10 and the top board 33 may be configured to be movable. In addition, the medical image generation apparatus 100A may be an apparatus in which the test object P is scanned in a standing position or sitting position. In this case, the medical image generation apparatus 100A has a test object supporting mechanism instead of the bed device 30 and the frame device 10 rotates the rotating frame 17 in an axial direction perpendicular to the floor face.

The console device 40 includes a memory 41, a display 42, an input interface 43, a communication interface 44, and a processing circuit 50, for example. Although the console device 40 is separate from the frame device 10 in the embodiment, some or all of components of the console device 40 may be included in the frame device 10.

The memory 41 is implemented as, for example, a semiconductor memory element such as a RAM or a flash memory, a hard disk, an optical disc, or the like. The memory 41 stores detected data, projection data, reconstructed image data, CT image data, and the like, for example. Such data may be stored in an external memory which can communicate with the medical image generation apparatus 100A instead of the memory 41 (or in addition to the memory 41). A cloud server which manages the external memory controls the external memory by receiving a read/write request.

The display 42 displays various types of information. For example, the display 42 displays a medical image (CT image) generated by the processing circuit, a GUT image through which various operations are received from an operator, and the like. The display 42 is a liquid crystal display, a CRT, an organic EL display, or the like, for example. The display 42 may be provided in the frame device 10. The display 42 may be a desk-top type or a display device (e.g., a tablet terminal) which can wirelessly communicate with the main body of the console device 40.

The input interface 43 receives various input operations from an operator and outputs electrical signals indicating the contents of the received input operations to the processing circuit 50. For example, the input interface 43 receives input operations such as collection conditions when detected data or projection data (which will be described later) are collected, reconstruction conditions when a CT image is reconstructed, and image processing conditions when a post-processed image is generated from a CT image. For example, the input interface 43 is implemented as a mouse, a keyboard, a touch panel, a trackball, a switch, a button, a joystick, a camera, an infrared sensor, a microphone, or the like. The input interface 43 may be provided in the frame device 10. In addition, the input interface 43 may be implemented as a display device (e.g., a tablet terminal) which can wirelessly communicate with the main body of the console device 40.

The communication interface 44 includes a communication interface such as an NIC, for example. The communication interface 44 communicates with the medical image processing apparatus 200 through the network NW and receives information from the medical image processing apparatus 200. The communication interface 44 outputs the received information to the processing circuit 50. Further, the communication interface 44 may transmit information to other devices connected through the network NW under the control of the processing circuit 50.

The processing circuit 50 controls the overall operation of the medical image generation apparatus 100A. The processing circuit 50 executes a system control function 51, a pre-processing function 52, a communication control function 53, an image processing function 54, a scan control function 55, a display control function 56, and the like, for example. Such components are implemented as a hardware processor such as a CPU executing a program (software). Some or all of such components may be implemented as hardware (circuit part including circuitry) such as an LSI, an ASIC, an FPGA, or a GPU or software and hardware in cooperation. The program may be stored in a non-transitory storage device such as the memory 41 in advance or stored in a detachable non-transitory storage medium such as a DVD or a CD-ROM and installed from the storage medium by mounting the storage medium in a drive device.

The components included in the console device 40 or the processing circuit 50 may be distributed and implemented as a plurality of hardware units. The processing circuit 50 may be implemented as a processing device which can communicate with the console device 40 instead of being a component included in the console device 40. The processing device is a work station connected to one X-ray CT apparatus or a device (e.g., a cloud server) which is connected to a plurality of X-ray CT apparatuses and collectively performs batch processes equivalent to those of the processing circuit 50 which will be described below.

The system control function 51 controls various functions of the processing circuit 50 basis on input operations received by the input interface 43.

The pre-processing function 52 performs pre-processing such as logarithmic conversion processing and offset correction processing, processing of correcting sensitivity between channels, or beam hardening correction on detected data output from the DAS 16 to generate projection data and stores the generated projection data in the memory 41.

When projection data is generated by the pre-processing function 52, the communication control function 53 causes the communication interface 44 to communicate with the medical image processing apparatus 200 and transmits the projection data to the medical image processing apparatus 200 that is a communication partner. In addition, the communication control function 53 causes the communication interface 44 to communicate with the medical image processing apparatus 200 and acquires a reconstructed image of a CT image from the medical image processing apparatus 200 that is the communication partner. When the reconstructed image of the CT image is acquired, the communication control function 53 may output the reconstructed image to the display 126. Accordingly, the reconstructed image is displayed on the display 126.

The image processing function 54 converts CT image data into three-dimensional image data or cross-sectional image data with an arbitrary cross section through a known method basis on an input operation received through the input interface 43 when the communication control function 53 acquires the reconstructed image of the CT image. Conversion into the three-dimensional image data may be performed by the pre-processing function 52.

The scan control function 55 controls detected data collection processing in the frame device 10 by instructing the X-ray high-voltage device 14, the DAS 16, the control device 18 and the bed driving device 32. The scan control function 55 controls photographing for collecting positioning images, and the operation of each part when an image used for diagnosis is captured.

The display control function 56 causes the display 126 to display the reconstructed image of the CT image acquired by the communication control function 53 or causes the display 126 to display the three-dimensional image data or cross-sectional image data converted from the CT image by the image processing function 54.

According to the aforementioned configuration, the medical image generation apparatus 100A scans the test object P in a mode such as helical scan, conventional scan, or step-and-shoot. The helical scan is a mode of rotating the rotating frame 17 while moving the top board 33 to helically scan the test object P. The conventional scan is a mode of rotating the rotating frame 17 with the top board 33 stopped to scan the test object P on a circular orbit. The conventional scan is executed. The step-and-shoot is a mode of moving the position of the top board 33 at certain intervals to perform the conventional scan in a plurality of scan areas.

The acquisition function 212 of the medical image processing apparatus 200 in the fourth embodiment causes the communication interface 202 to communicate with the medical image generation apparatus 100A that is the X-ray CT apparatus to acquire projection data from the medical image generation apparatus 100A. For example, when the medical image generation apparatus 100A has imaged the test object OB through helical scan or conventional scan, projection data becomes non-Cartesian data in which sample points are not arranged in a grid form with respect to a grid of a three-dimensional coordinate system in which reconstruction is performed. Hereinafter, a description will be provided on the assumption that projection data is non-Cartesian data. Non-Cartesian projection data is represented by a vector having each sample point as an element like the non-Cartesian k-space data Dk.

The reconstruction processing function 214 reconstructs a CT image from non-Cartesian projection data acquired by the acquisition function 212 according to the medical image reconstruction model 300 indicated by the medical image reconstruction model information 232.

Figure 17:
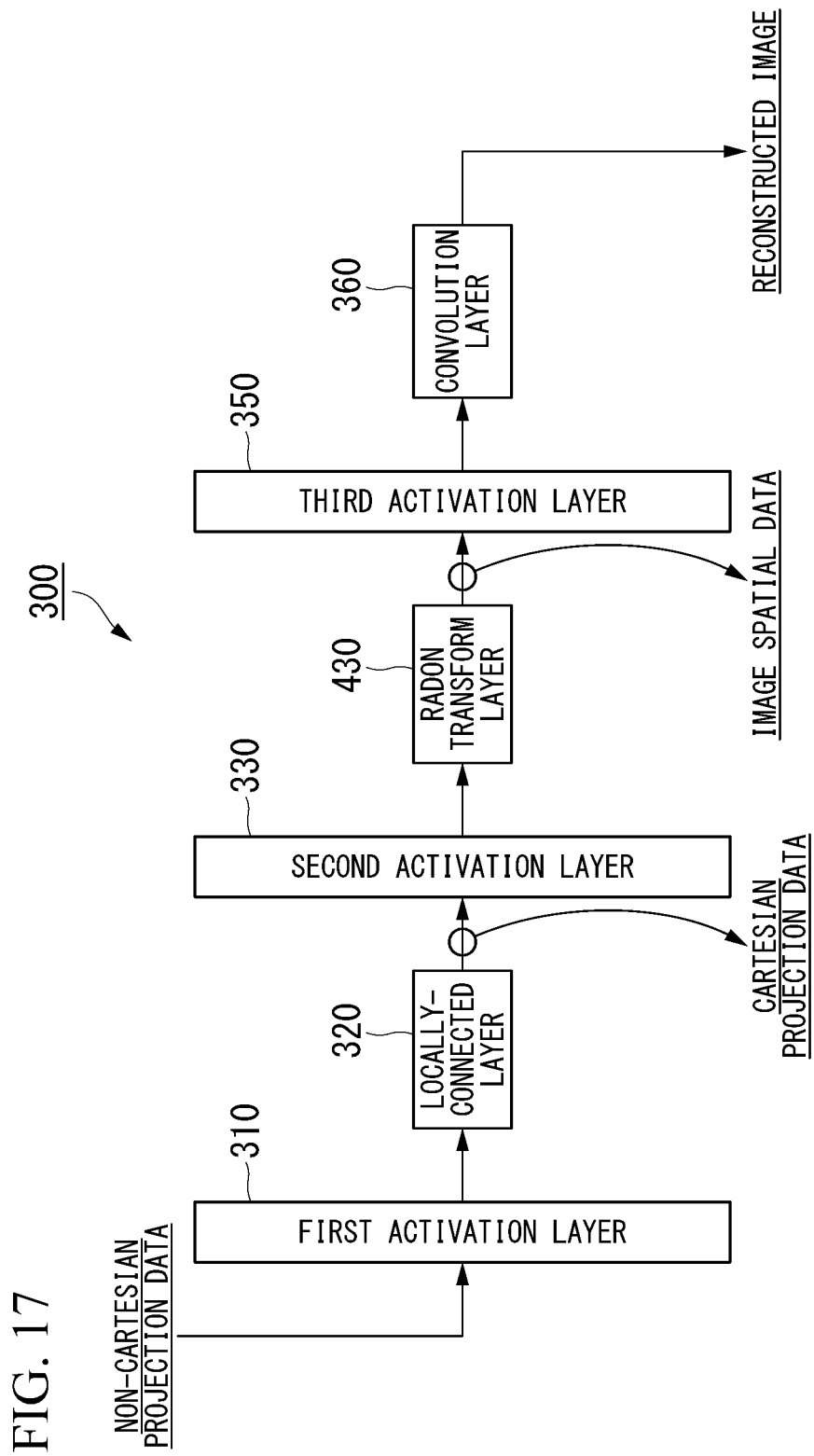
FIG. 17 is a diagram showing an example of a medical image reconstruction model according to the fourth embodiment.

FIG. 17 is a diagram showing an example of the medical image reconstruction model 300 in the fourth embodiment. As shown, the medical image reconstruction model 300 in the fourth embodiment includes the first activation layer 310, the locally-connected layer 320, the second activation layer 330, a Radon transform layer 430, the third activation layer 350 and the convolution layer 360, for example.

A vector indicating non-Cartesian projection data acquired through the acquisition function 212 is input to the first activation layer 310 in the fourth embodiment. The first activation layer 310 performs pooling processing or activation function calculation processing on the vector of the input non-Cartesian projection data and outputs the resultant vector to the locally-connected layer 320.

When the vector of the non-Cartesian projection data is input from the first activation layer 310, the locally-connected layer 320 in the fourth embodiment multiplies the vector by a coefficient matrix L including a plurality of coefficient sequences C. Specifically, the locally-connected layer 320 calculates a product-sum of each element of the vector of the non-Cartesian projection data and each coefficient sequence C and generates a vector including a plurality of elements with which the product-sums are associated as element values as Cartesian projection data.

The locally-connected layer 320 outputs the generated Cartesian projection data to the second activation layer 330.

The vector of the Cartesian projection data is input from the locally-connected layer 320 to the second activation layer 330 in the fourth embodiment. The second activation layer 330 performs pooling processing or activation function calculation processing on the input vector and outputs the resultant vector to the Radon transform layer 430.

The Radon transform layer 430 performs a transform corresponding to an inverse process of Radon transform on the vector of the Cartesian projection data input from the second activation layer 330. The transform corresponding to the inverse process of Radon transform may be filtered back projection or filter-free back projection, for example. The Radon transform layer 430 outputs a vector obtained by applying the transform corresponding to the inverse process of Radon transform to the vector of the Cartesian projection data input to the third activation layer 350. The vector obtained by applying the transform corresponding to the inverse process of Radon transform to the vector of the Cartesian projection data represents image spatial data in which pixel values are associated with physical positional coordinates.

The vector on which the transform corresponding to the inverse process of Radon transform has been performed, that is, the image spatial data, is input from the Radon transform layer 430 to the third activation layer 350 in the fourth embodiment. The third activation layer 350 performs pooling processing or activation function calculation processing on the input image spatial data and outputs the resultant vector to the convolution layer 360.

When the vector of the image spatial data is input from the third activation layer 350, the convolution layer 360 in the fourth embodiment repeats product-sum calculation for the input vector while sliding a linear transformation matrix with a certain determined stride amount and generates, from the vector of the input image spatial data, a vector including a plurality of elements with which product-sums with respect to the linear transformation matrix are associated as element values. Then, the convolution layer 360 outputs the generated vector as a reconstructed image of a CT image.

The output control function 216 in the fourth embodiment transmits the reconstructed image of the CT image output from the convolution layer 360 to the medical image generation apparatus 100A connected through the communication interface 202, for example. In addition, the output control function 216 may cause the display 206 to output (display) the reconstructed image of the CT image.

According to the above-described fourth embodiment, it is possible to improve the accuracy of reconstruction of a CT image to generate a medical image with high picture quality through reconstruction by including the acquisition function 212 which acquires non-Cartesian projection data generated by applying X-ray to the test object OB form the medical image generation apparatus 100A, the locally-connected layer 320 which derives product-sums of the acquired non-Cartesian projection data and a plurality of coefficient sequences C and generates a vector including a plurality of elements with which the product-sums derived for the coefficient sequences C are associated as element values as Cartesian projection data, the Radon transform layer 430 which performs a transform corresponding to an inverse process of Radon transform on the generated Cartesian projection data, and the convolution layer 360 which generates an image including a plurality of pixels with which product-sums obtained by multiplying the Cartesian projection data on which the transform corresponding to the inverse process of Radon transform has been performed by a linear transformation matrix are associated as pixel values as a reconstructed image of a CT image.

Any of the above-described embodiments can be represented as follows.

A medical image processing apparatus including:
a storage which stores a program, and
a processor,
wherein the processor is configured to execute the program:
to execute the program to acquire non-Cartesian data generated by applying electromagnetic waves to a test object;
to derive product-sums of the acquired non-Cartesian data and a plurality of coefficient sets;
to generate Cartesian data including a plurality of elements with which the product-sums for the coefficient sets are associated as element values; and
to reconstruct a medical image in which at least part of the test object has been imaged basis on the generated Cartesian data.

According to at least one of the above-described embodiments, it is possible to improve the accuracy of reconstruction of a medical image to generate a medical image with high picture quality through reconstruction by including the acquisition function 212 which acquires non-Cartesian k-space data Dk generated by applying magnetic fields to the test object OB from the medical image generation apparatus 100, the locally-connected layer 320 which derives product-sums of the acquired non-Cartesian k-space data Dk and a plurality of coefficient sequences C and generates a vector including a plurality of elements with which the product-sums derived for the coefficient sequences C are associated as element values as Cartesian k-space data Dk, the Fourier transform layer 340 which performs a Fourier transform or an inverse Fourier transform on the generated Cartesian k-space data Dk, and the convolution layer 360 which generates an image including a plurality of pixels with which product-sums obtained by multiplying the Fourier transformed or inversely Fourier transformed Cartesian k-space data Dk by a linear connection matrix are associated as pixel values as a reconstructed image of an MR image.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image processing apparatus, comprising:
processing circuitry configured to acquire non-Cartesian data from a test object;
derive product-sums of the non-Cartesian data and a plurality of coefficient sets;
generate Cartesian data including a plurality of elements with which the product-sums derived for the coefficient sets are associated as element values; and
generate a medical image in which at least part of the test object has been imaged through reconstruction based on the generated Cartesian data,
wherein the processing circuitry is further configured to
acquire the non-Cartesian data, which is generated by applying magnetic fields to the test object;
derive the product-sums of the non-Cartesian data and the plurality of coefficient sets;
generate the Cartesian data including the plurality of elements with which the product-sums derived for the coefficient sets are associated as the element values; and
generate the medical image by performing a Fourier transform or an inverse Fourier transform on the Cartesian data and multiplying the Cartesian data on which the Fourier transform or the inverse Fourier transform has been performed by a linear connection matrix.

2. The medical image processing apparatus according to claim 1, wherein the non-Cartesian data is a set of a plurality of pieces of sample data included in a frequency space corresponding to a space in which the test object is present, and the processing circuitry is further configured to generate the Cartesian data by multiplying the non-Cartesian data by a matrix including the coefficient sets learned in advance, depending on a position of the sample data in the frequency space.

3. The medical image processing apparatus according to claim 1, wherein the processing circuitry is further configured to
acquire the non-Cartesian data, which is generated by applying radiation to the test object,
derive the product-sums of the non-Cartesian data and the plurality of coefficient sets,
generate the Cartesian data including the plurality of elements with which the product-sums derived for the coefficient sets are associated as the element values, and
generate the medical image by performing a transform corresponding to an inverse process of a Radon transform on the Cartesian data and multiplying the Cartesian data on which the transform corresponding to the inverse process of a Radon transform has been performed by a linear connection matrix.

4. The medical image processing apparatus according to claim 1, wherein the processing circuitry is further configured to derive the product-sums of the Cartesian data and the plurality of coefficient sets,
generate second Cartesian data including the plurality of elements with which the product-sums derived for the coefficient sets are associated as the element values, and
generate the medical image based on the generated second Cartesian data.

5. The medical image processing apparatus according to claim 1, wherein the processing circuitry is further configured to:
change a resolution of the non-Cartesian data,
derive the product-sums of the non-Cartesian data, which has the changed resolution, and the plurality of coefficient sets, and
generate the Cartesian data including the plurality of elements with which the product-sums derived for the coefficient sets are associated as the element values.

6. A medical image generation apparatus, comprising:
processing circuitry configured to
generate non-Cartesian data by applying electromagnetic waves to a test object;
derive product-sums of the non-Cartesian data and a plurality of coefficient sets;

generate Cartesian data including a plurality of elements with which the product sums derived for the coefficient sets are associated as element values; and generate a medical image in which at least part of the test object has been imaged through reconstruction based on the generated Cartesian data, wherein the processing circuitry is further configured to acquire the non-Cartesian data, which is generated by applying magnetic fields to the test object;

derive the product-sums of the non-Cartesian data and the plurality of coefficient sets;

generate the Cartesian data including the plurality of elements with which the product-sums derived for the coefficient sets are associated as the element values; and generate the medical image by performing a Fourier transform or an inverse Fourier transform on the Cartesian data and multiplying the Cartesian data on which the Fourier transform or the inverse Fourier transform has been performed by a linear connection matrix.

7. A medical image processing method, comprising:

acquiring, by processing circuitry, non-Cartesian data from a test object;

deriving product-sums of the acquired non-Cartesian data and a plurality of coefficient sets;

generating Cartesian data including a plurality of elements with which the product-sums derived for the coefficient sets are associated as element values; and generating a medical image in which at least part of the test object has been imaged through reconstruction based on the generated Cartesian data, wherein the method further includes acquiring the non-Cartesian data, which is generated by applying magnetic fields to the test object;

deriving the product-sums of the non-Cartesian data and the plurality of coefficient sets;

generating the Cartesian data including the plurality of elements with which the product-sums derived for the coefficient sets are associated as the element values; and generating the medical image by performing a Fourier transform or an inverse Fourier transform on the Cartesian data and multiplying the Cartesian data on which the Fourier transform or the inverse Fourier transform has been performed by a linear connection matrix.

8. A non-transitory computer-readable non-transitory storage medium storing a program that, when executed, causes a computer to execute a method comprising:

acquiring non-Cartesian data from a test object;

deriving product-sums of the acquired non-Cartesian data and a plurality of coefficient sets;

generating Cartesian data including a plurality of elements with which the product-sums derived for the coefficient sets are associated as element values; and generating a medical image in which at least part of the test object has been imaged through reconstruction based on the generated Cartesian data, wherein the method further includes acquiring the non-Cartesian data, which is generated by applying magnetic fields to the test object;

deriving the product-sums of the non-Cartesian data and the plurality of coefficient sets;

generating the Cartesian data including the plurality of elements with which the product-sums derived for the coefficient sets are associated as the element values; and generating the medical image by performing a Fourier transform or an inverse Fourier transform on the Cartesian data and multiplying the Cartesian data on which the Fourier transform or the inverse Fourier transform has been performed by a linear connection matrix.

9. The medical image processing apparatus according to claim 2, wherein the processing circuitry is further configured to generate the Cartesian data by multiplying the non-Cartesian data by a matrix including the coefficient sets generated by learning a relationship between a value indicated by the sample data and the position where the sample data is acquired in the frequency space using training data, the training data being a data set in which a medical image is associated with non-Cartesian data as correct answer data.

10. The medical image processing apparatus according to claim 9, wherein the training data is a data set in which a second medical image reconstructed from a second non-Cartesian data is associated with the second non-Cartesian data as the correct answer data, the second non-Cartesian data being non-Cartesian data with a larger number of sample data than first non-Cartesian data, which is the non-Cartesian data acquired from the test object.

11. The medical image processing apparatus according to claim 9, wherein the training data is a data set in which a third medical image is associated with third non-Cartesian data, which is non-Cartesian data obtained by performing sampling simulation on the third medical image, as the correct answer data.

* * * * *